(12) United States Patent
O'Toole et al.

(10) Patent No.: US 12,318,531 B2
(45) Date of Patent: Jun. 3, 2025

(54) PASSIVE MILK COLLECTION VESSEL

(71) Applicant: Chiaro Technology Limited, London (GB)

(72) Inventors: Jonathan O'Toole, Bristol (GB); Andrew Carr, Edinburgh (GB); Nick Sardar, London (GB); Clare Larkspur, Bristol (GB); Paul Reid, Bristol (GB); Emma Morris, Bristol (GB); Edward Sims, Bristol (GB)

(73) Assignee: Chiaro Technology Limited, London (GB)

( * ) Notice: Subject to any disclaimer, the term of this patent is extended or adjusted under 35 U.S.C. 154(b) by 504 days.

(21) Appl. No.: 17/756,265

(22) PCT Filed: Nov. 19, 2020

(86) PCT No.: PCT/GB2020/052955
§ 371 (c)(1),
(2) Date: May 20, 2022

(87) PCT Pub. No.: WO2021/099790
PCT Pub. Date: May 27, 2021

(65) Prior Publication Data
US 2022/0401639 A1    Dec. 22, 2022

(30) Foreign Application Priority Data

Nov. 22, 2019   (GB) .................................... 1917017
Oct. 7, 2020    (GB) .................................... 2015917

(51) Int. Cl.
*A61M 1/00*   (2006.01)
*A41C 3/04*   (2006.01)
*A61M 1/06*   (2006.01)

(52) U.S. Cl.
CPC ............. *A61M 1/69* (2021.05); *A41C 3/04* (2013.01); *A61M 1/067* (2021.05)

(58) Field of Classification Search
CPC ............ A61M 1/69; A61M 1/067; A41C 3/04
See application file for complete search history.

(56) References Cited

U.S. PATENT DOCUMENTS 3,840,012 A * 10/1974 Rushton, Jr. .......... A61M 1/062
                                                        450/37
4,270,538 A *  6/1981 Murphy ................ A61M 1/062
                                                        450/37

(Continued)

OTHER PUBLICATIONS

International Search Report issued in International Application No. PCT/GB2020/052955, mailed Mar. 16, 2021, two pages.

*Primary Examiner* — Guy K Townsend
(74) *Attorney, Agent, or Firm* — Sterne, Kessler, Goldstein & Fox P.L.L.C.

(57) ABSTRACT

A passive milk collection device for storing milk comprises a flexible inner member including a nipple hole for receiving a nipple, and in which, in use, part of the rear surface of the inner member is configured to securely seal onto a user's breast. The device includes a removable rigid outer member configured to attach onto the front surface of the inner member and to provide a free air space around the nipple area for storing milk from the nipple. The circumference of the outer edge of the rear surface of the flexible inner member is substantially larger than the circumference of the rigid outer member.

20 Claims, 30 Drawing Sheets

(56) References Cited

U.S. PATENT DOCUMENTS

| | | | | |
|---|---|---|---|---|
| 7,662,018 | B1* | 2/2010 | Thompson | A61J 13/00 |
| | | | | 604/74 |
| 7,785,305 | B2* | 8/2010 | Myers | A61M 1/062 |
| | | | | 604/74 |
| 8,720,713 | B2* | 5/2014 | Olshansky | A61F 15/001 |
| | | | | 220/4.23 |
| 10,016,566 | B2* | 7/2018 | Zhang | A61M 35/00 |
| 10,744,025 | B2* | 8/2020 | Osorio | A61F 5/4407 |
| 11,806,453 | B2* | 11/2023 | Alvarez | A61M 1/06935 |
| 2002/0193731 | A1* | 12/2002 | Myers | A61M 1/062 |
| | | | | 206/427 |
| 2005/0234370 | A1* | 10/2005 | Beal | A61M 1/06 |
| | | | | 604/74 |
| 2006/0106334 | A1* | 5/2006 | Jordan | A61M 1/062 |
| | | | | 604/74 |
| 2007/0219486 | A1* | 9/2007 | Myers | A61M 1/067 |
| | | | | 604/74 |
| 2008/0208116 | A1* | 8/2008 | Dao | A61M 1/064 |
| | | | | 604/74 |
| 2008/0262420 | A1* | 10/2008 | Dao | A61M 1/067 |
| | | | | 604/74 |
| 2010/0130921 | A1* | 5/2010 | Kobayashi | A61M 1/06 |
| | | | | 604/74 |
| 2014/0236072 | A1* | 8/2014 | Zhang | A61M 1/06 |
| | | | | 604/23 |
| 2015/0217033 | A1* | 8/2015 | Pollen | A61M 1/062 |
| | | | | 604/74 |
| 2016/0206794 | A1* | 7/2016 | Makower | A61M 1/066 |
| 2016/0296682 | A1* | 10/2016 | Phillips | A61M 1/067 |
| 2018/0333523 | A1* | 11/2018 | Chang | A61M 1/06935 |
| 2018/0353320 | A1* | 12/2018 | Osorio | A61F 5/4407 |
| 2020/0383823 | A1* | 12/2020 | Osorio | A61F 5/4408 |

* cited by examiner

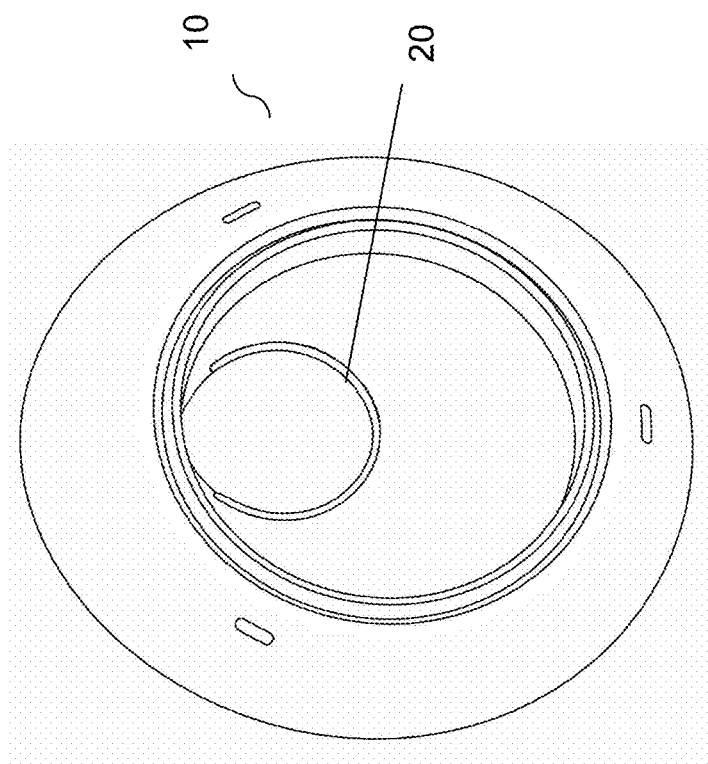
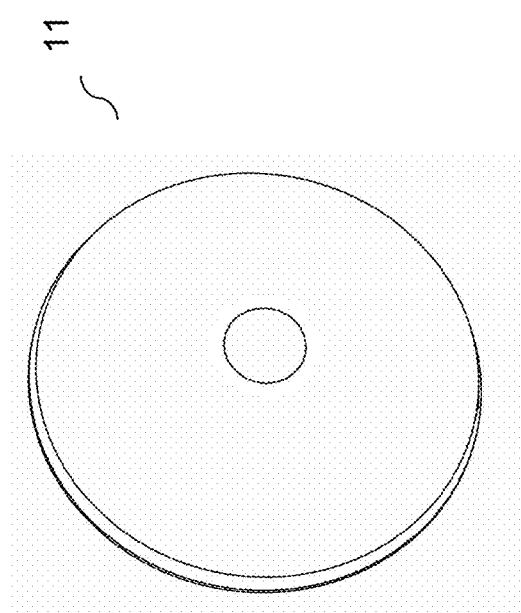
FIGURE 3

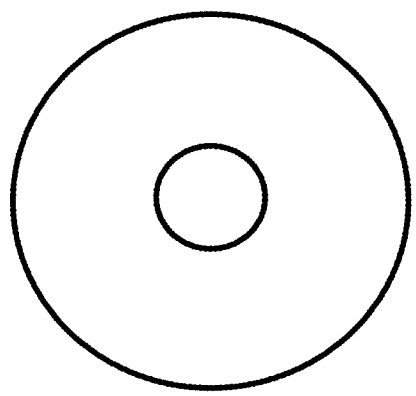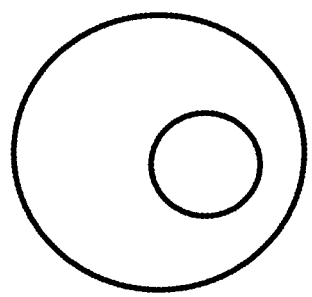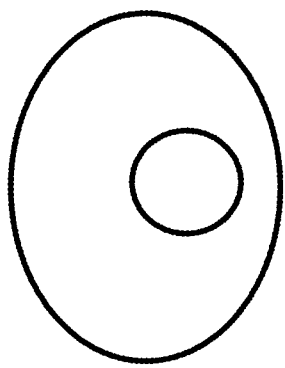
FIGURE 13

PASSIVE MILK COLLECTION VESSEL

BACKGROUND OF THE INVENTION

1. Field of the Invention

The field of the invention relates to a passive milk collection vessel.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Description of the Prior Art

Collection shells are often worn during breastfeeding or in between feeds in order to collect any leaking milk or milk let-down.

Additionally, they can also be used to protect the nipple and alleviate some discomfort due to sensitive or irritated nipples.

However, conventional shells have a number of disadvantages, such as being susceptible to leaks, not being discreet enough and providing some discomfort to the mother.

SUMMARY OF THE INVENTION

The invention relates to an improved wearable passive milk collection vessel.

An aspect of the invention is a passive milk collection device for storing milk. The device comprises a flexible inner member including a nipple hole for receiving a nipple, and in which, in use, part of the rear surface of the inner member is configured to securely seal onto a user's breast; and a removable rigid outer member configured to attach onto the front surface of the inner member and to provide a free air space around the nipple area for storing milk from the nipple. The circumference of the outer edge of the rear surface of the flexible inner member is substantially larger than the circumference of the rigid outer member.

BRIEF DESCRIPTION OF THE FIGURES

Aspects of the invention will now be described, by way of example(s), with reference to the following Figures, which each show features of various implementations of the invention including optional features that may be utilised:

FIG. 3 is an outer member and inner member of a passive milk collection vessel shown side by side.

FIG. 13 shows front views of the passive milk collection vessel with varying form factor.

DETAILED DESCRIPTION

Figure 1:
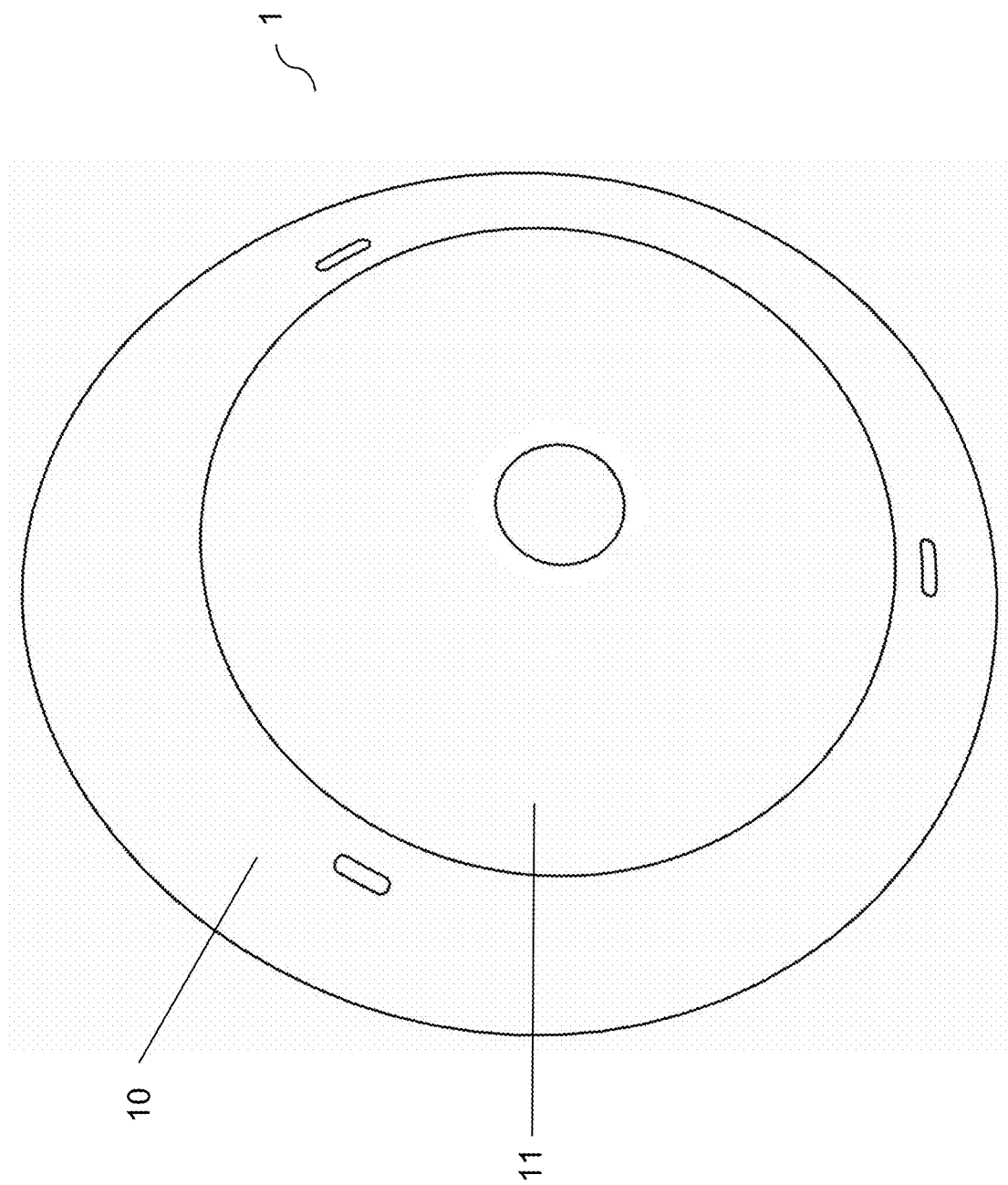
FIG. 1 is a perspective view of a passive milk collection vessel.
Figure 2:
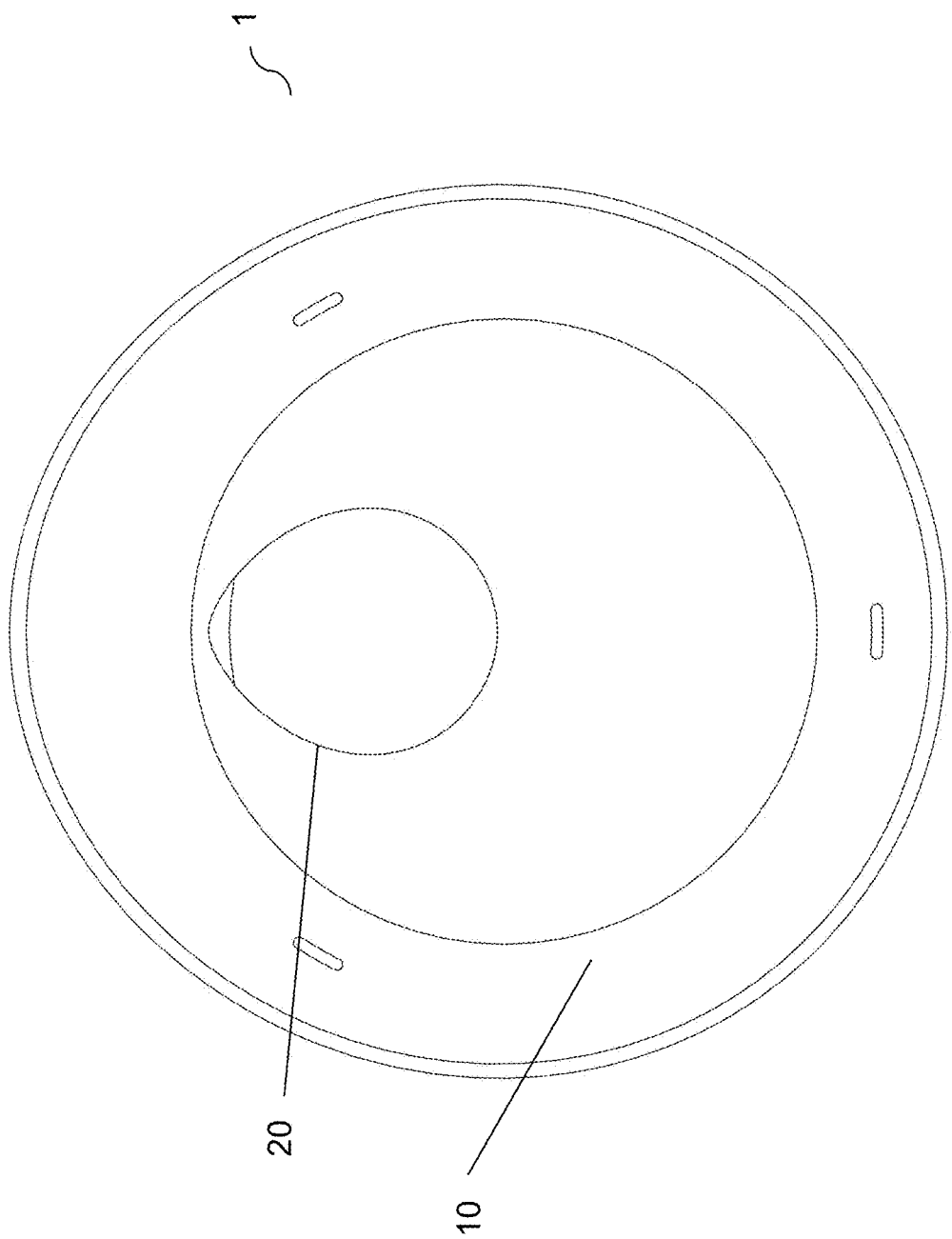
FIG. 2 is a back view of a passive milk collection vessel.

With reference to FIGS. 1 and 2, a perspective view and back view of a passive milk collection vessel or device are respectively shown. The device comprises a flexible inner member or skirt 10 which contacts the user's breast and a removable rigid outer member 11, which faces outwards from the breast. The rear surface of the inner member 10 includes an opening or nipple hole 20 for receiving a nipple. Thanks to the elasticity of the inner member 10, a comfortable seal is formed between the rear surface of the device and the user's breast. In addition, the inner member 10 has an asymmetrical ergonomic shape providing a secure fit. The form-factor of the design is configured to minimize visibility of the device when worn under clothes. By providing an uninterrupted or continuous contour with the breast, the passive milk collection vessel is very discreet and is also almost invisible or substantially invisible when worn under clothes. As a result, the passive milk collection vessel is also held comfortably inside a bra.

The passive milk collection vessel is configured to securely hold itself in place on the breast due to the flexibility and elasticity of the inner member 10. This prevents possible leaking of any milk let-down outside the milk collection vessel and provides mothers the confidence of being able to wear any clothing they wish in between pumps or in between feeds.

Alternatively, the inner member includes a 'flippable' or bendable portion that is configured to securely seal or self-seal onto at least part of the breast around the nipple area via the creation of low negative pressure inside the passive milk collection vessel. The passive milk collection device may then be worn temporarily without a bra or for a long time period with a bra.

A user can wear one device at a time, or one device on each breast at the same time. One intended use case is that the user places the device onto their nipple in-bra and wears the device for up to 3 hours at a time.

With reference to FIG. 3, the outer member 11 and inner flexible member 10 are shown side by side.

The shape of the flexible inner member or skirt 10, seen from the front, is not circular, but slightly elongated at the top and slightly truncated at its base. Seen from the side, the rear or outermost edge of the skirt 10 is not parallel with the rear edge of the central outer member 11, but instead the top of the rear or outermost edge of the skirt 10 is further away from the rear edge of the central outer member 11 than the bottom of the edge of the skirt 10. The flexible skirt 10 is hence shaped or configured to fit comfortably against the breast. Also, the long axis through the device (when looking at the device from the front) does not have to be vertical when the device is worn; the user can rotate the device before placing it against the breast so that the flexible skirt 10 fits even better against the breast.

Figure 4:
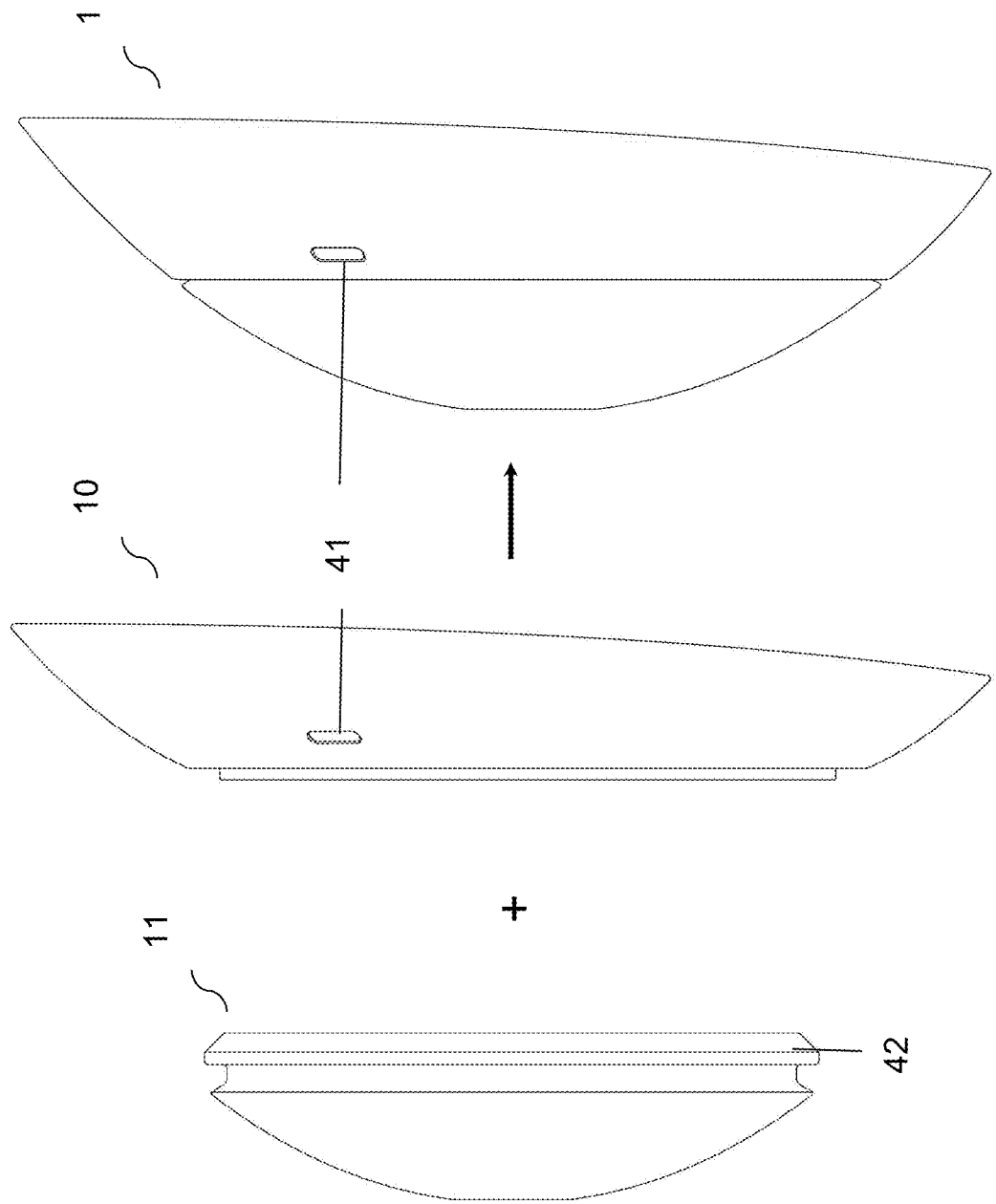
FIG. 4 is an outer member and inner member of a passive milk collection vessel shown side by side and assembled.

With reference to FIG. 4, the rigid outer member 11 and flexible member 10 are shown side by side and assembled.

The rigid outer member 11 has a convex outer surface and when assembled, the inner member 10 and outer member 11 form a chamber or vessel that is shaped to collect milk during let-down. The capacity of the chamber is approximately 1 US fluid ounce or 30 ml. Additionally, the chamber also provides a free air space around the nipple area for protecting the nipple and an area surrounding the nipple.

The nipple hole 20 has an asymmetrical shape or a teardrop-like shape providing an increased capacity of the vessel and a flexible orientation. The nipple hole 20 is also positioned and shaped to allow easy pouring of collected milk out of the device. When ready, the user removes the device from their breast, and decants any collected milk via the nipple hole into a storage device of their choice.

The inner member 10 includes one or more ventilation holes or openings 41 which may be plugged using an elastic feature built into the inner member 10 or a separate plugging member. Ventilation holes 41 provide comfort for the user when going about daily activities.

The two parts, namely the inner 10 and outer 11 members, push together and pull apart easily for hassle free assembly, disassembly and cleaning. Outer members 11 are therefore interchangeable.

The outer member 11 may be easily pressed or pushed into engagement with the inner member 10. The circular symmetry of the outer member 11 also means that the outer member can be assembled in any way onto the inner member 10. A bump feature 42 located around a periphery of the outer member is used to secure the outer member 11 onto the inner member 10.

Figure 5:
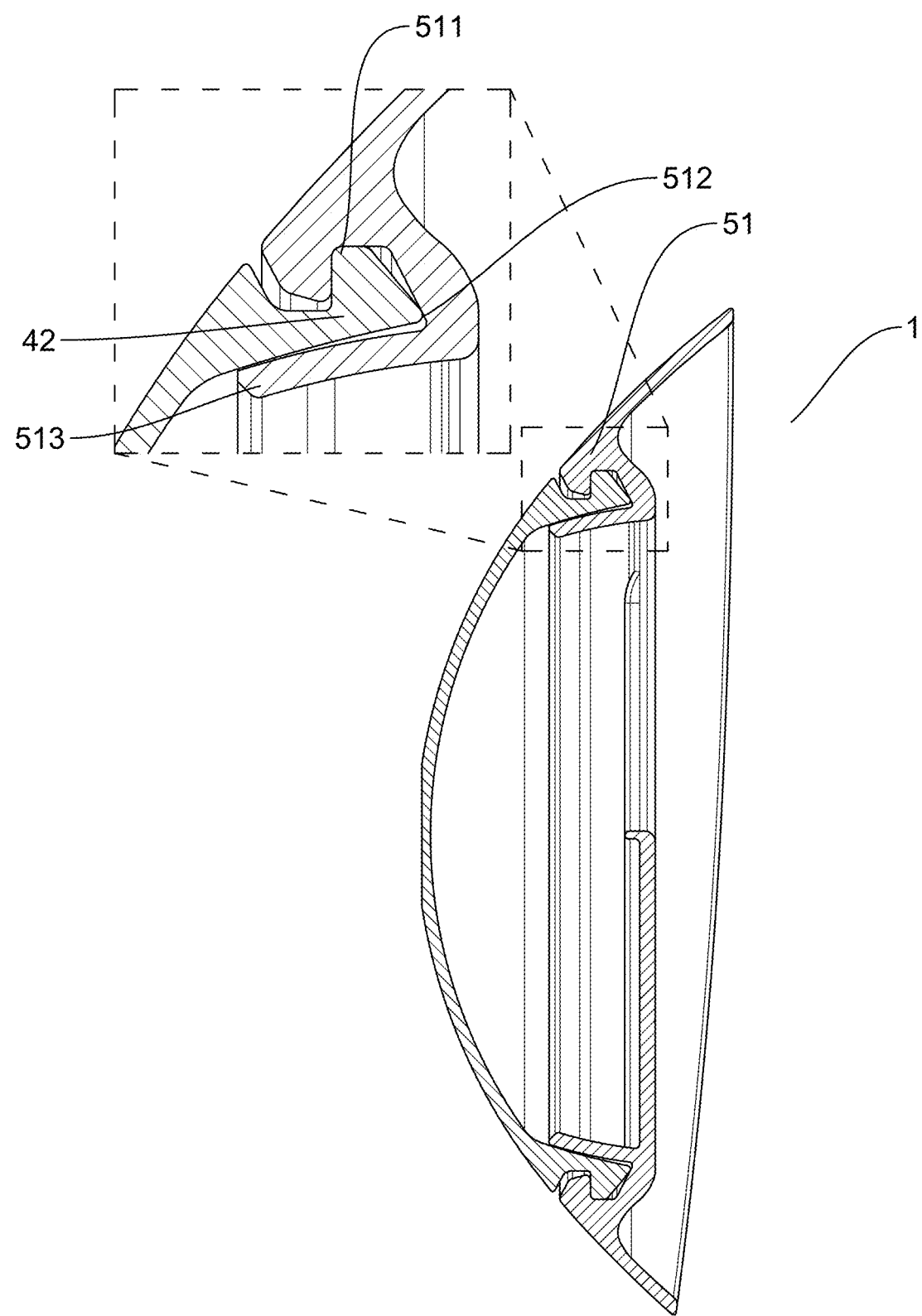
FIG. 5 is a side view of a passive milk collection vessel.

With reference to FIG. 5, the attachment mechanism between the rigid outer member 11 and the flexible inner member 10 is shown in detail. The bump feature 42 located on a periphery of the outer member 11 engages with a hook 51 located around a periphery of the inner member 10. As shown, this creates at least three sealing points on the hook: on the tip of the hook 511, on the base of the hook 512 and on the inner rim giving a triple seal protection 513.

This, in turns, provides a tight seal between the inner 10 and outer 11 members. Further, there is enough retention force ensuring that the outer member 11 does not come out from the inner member 10 during a user's normal daily activities.

In addition, the flexible inner member is moulded undersize and stretches to fit to the rigid outer member, thus ensuring an interference fit seal between the inner and outer members at the hook feature to always ensure a seal condition.

Figure 6:
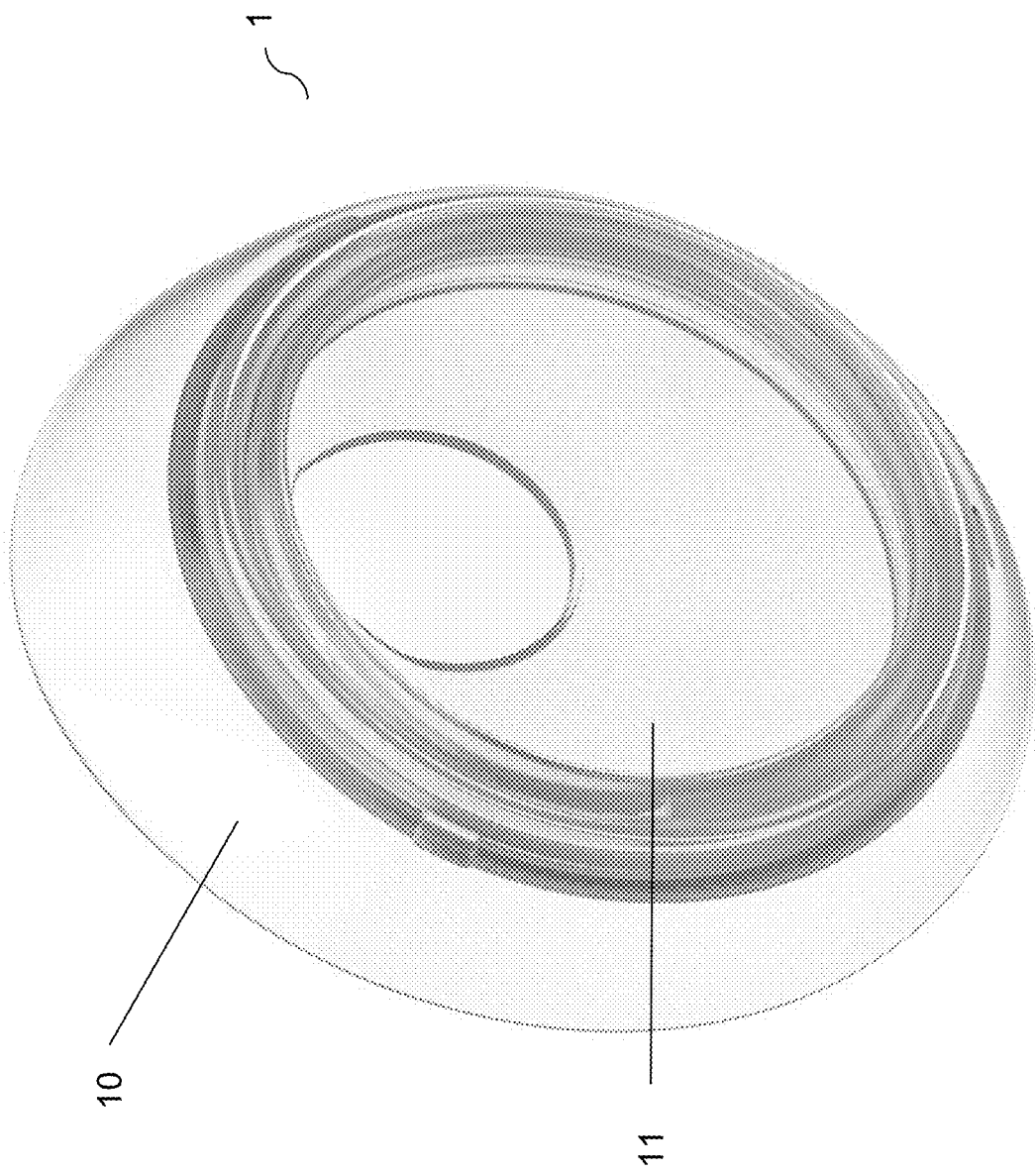
FIG. 6 is a perspective view of a rendering of a passive milk collection vessel.
Figure 7:
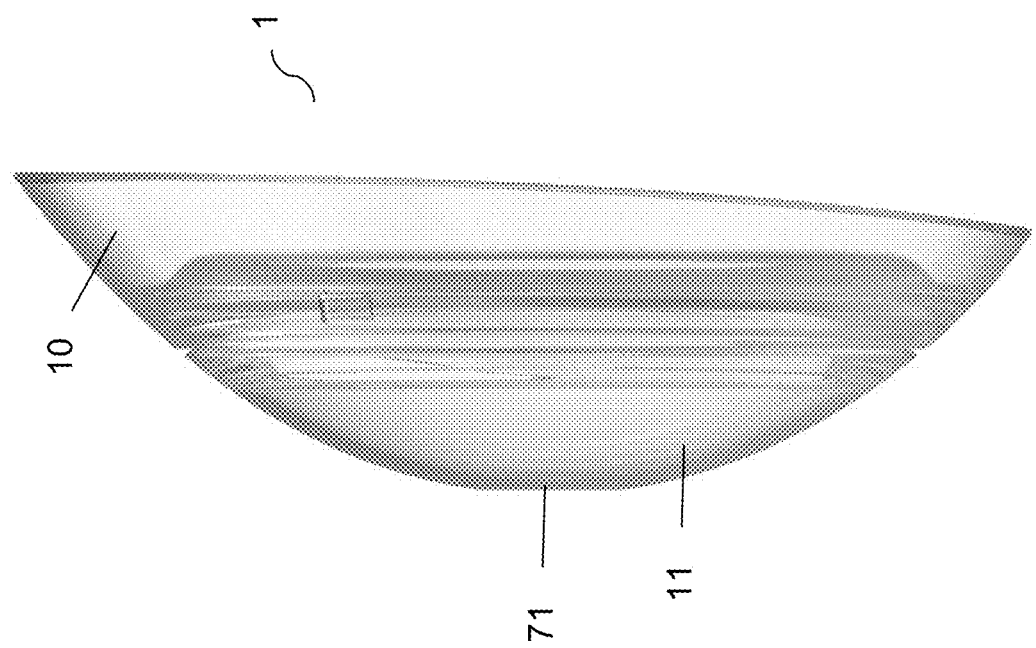
FIG. 7 is a side view of a rendering of a passive milk collection vessel.

With reference to FIGS. 6 and 7, a perspective view and a side view of a rendering of a passive milk collection vessel are shown. The entire device is substantially transparent or optically clear providing an unobstructed view of the breast or nipple area and a discreet look when worn with or without clothes. The inner member 10 is made of flexible silicone and the outer member 11 is made of hard plastic. The materials are chosen to provide ease of use and cleaning.

Alternatively, the entire device may also be skin coloured.

The front surface of the rigid outer member also includes a flat portion 71 so that the entire device can rest stably on its front on a surface; while preventing any milk spillage.

Figure 8:
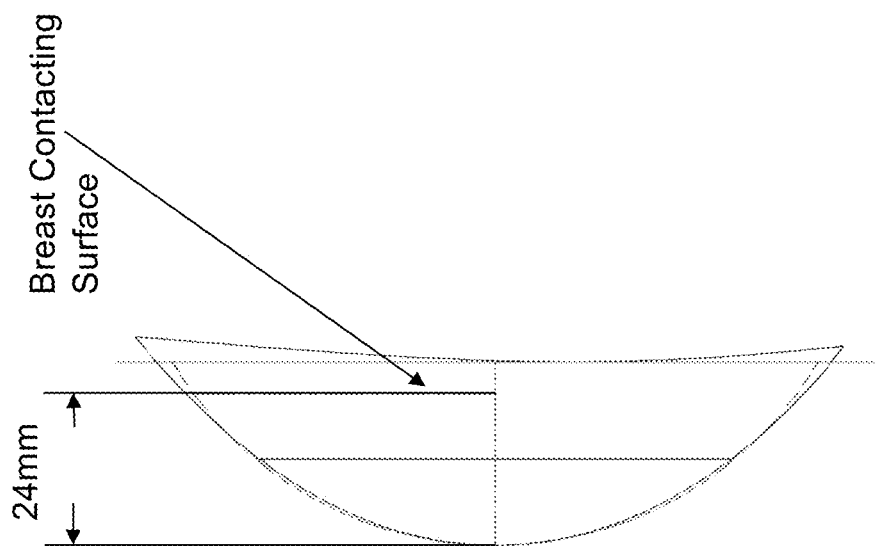
FIG. 8 is a side view of a rendering of a passive milk collection vessel.
Figure 9:
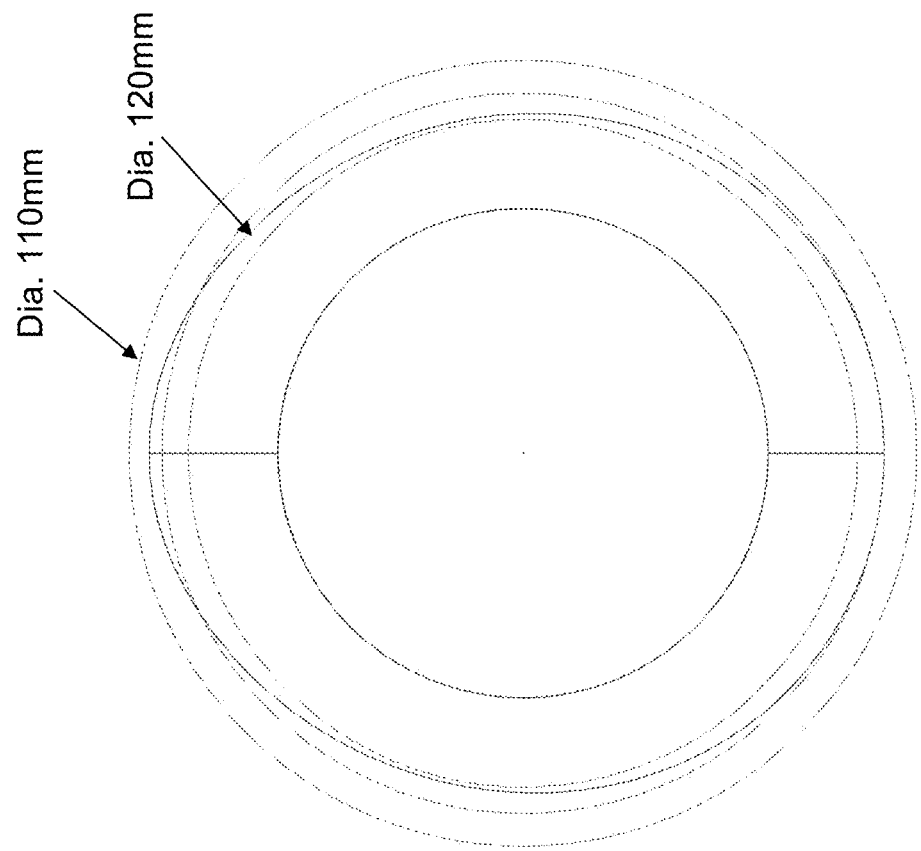
FIG. 9 is a side view of a front view of a passive milk collection vessel.

With reference to FIGS. 8 and 9, dimensions of the device are shown. The device is specifically shaped to provide a discreet profile, when worn.

Figure 10:
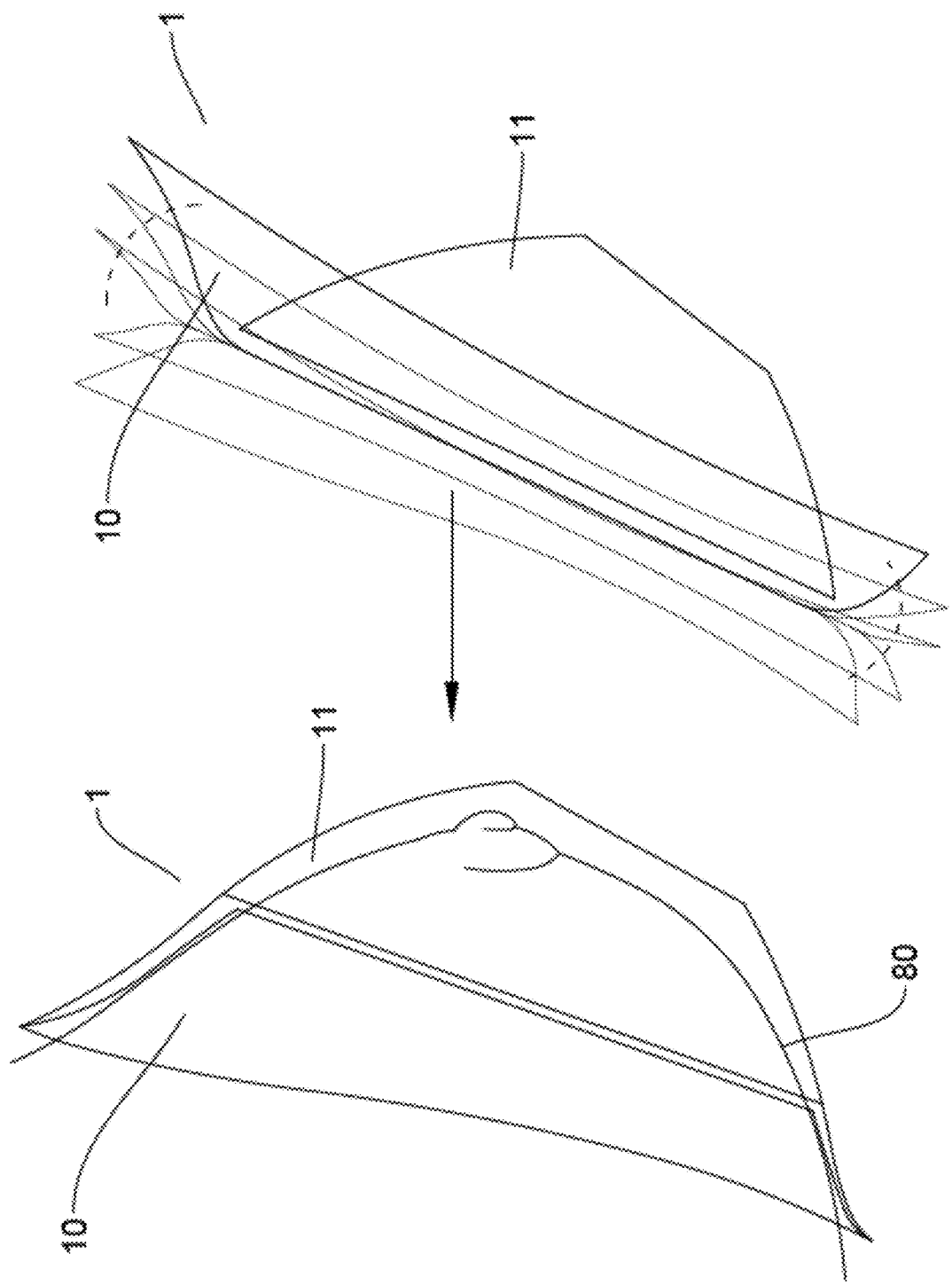
FIG. 10 is side views illustrating a passive milk collection vessel including a 'flippable' portion.

With reference to FIG. 10, drawings illustrate the flexible inner member including a 'flippable' portion as previously discussed above. The reversible 'flippable' feature, shown in grey shading, allows the user to attach the device on at least part of the breast 80. The 'flippable' portion is flipped onto the breast in order to help secure the device onto the breast, providing extra leak proof security. The device may then also be worn either with or without a bra.

Figure 11:
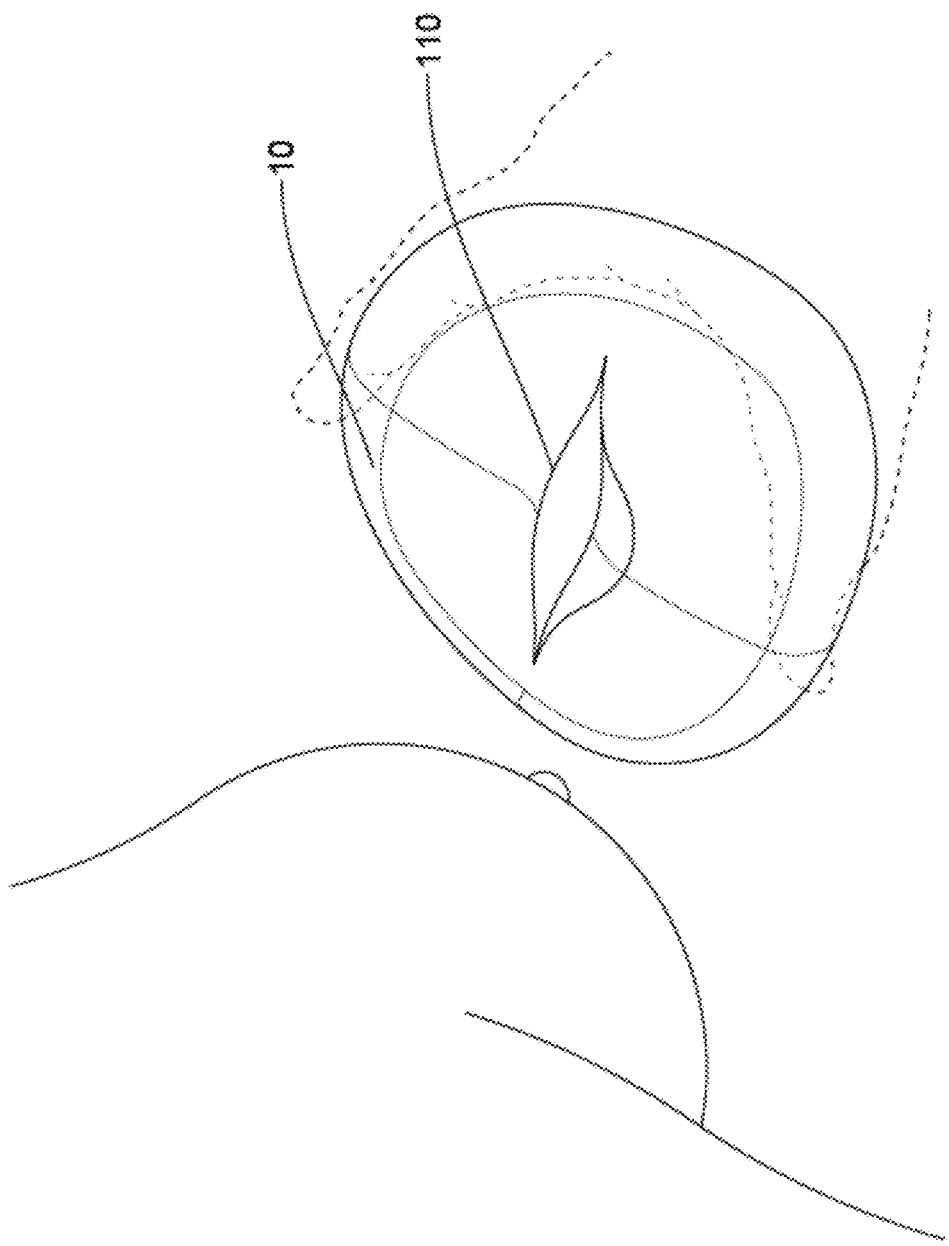
FIG. 11 is a figure illustrating a passive milk collection vessel including a non-drip barrier.

With reference to FIG. 11, the passive milk collection vessel is shown including a non-drip barrier. A slit 110 is located on the rear surface of the flexible inner member. When held in order to be placed onto the breast, as shown, the slit on the flexible inner member provides an opening to receive a nipple. When the device is removed from the breast, the slit closes and provides a non-drip barrier in order to prevent any milk spillage.

Figure 12:
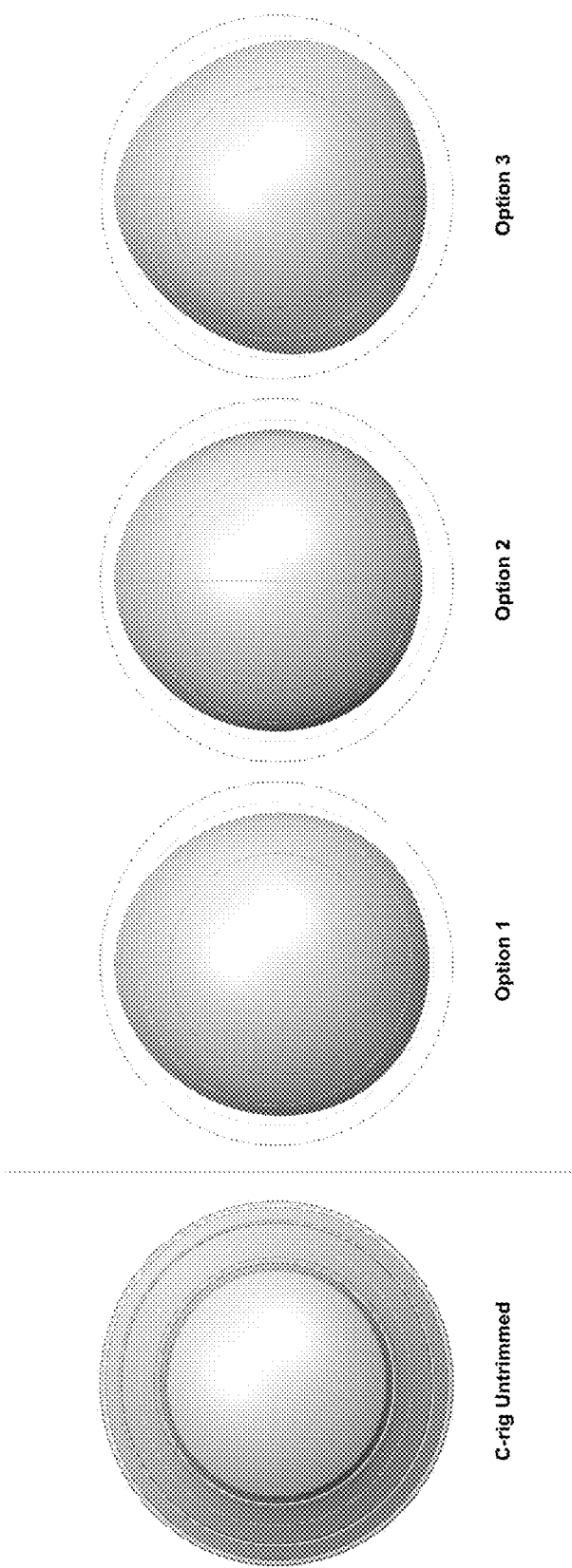
FIG. 12 shows front views of the passive milk collection vessel with varying form factor.

With reference to FIGS. 12 and 13, the passive milk collection vessel is shown with varying shapes and form factor. FIG. 13 also shows varying locations of the nipple hole on the flexible inner member.

With reference to FIGS. 14 to 19, further sealing solutions for sealing the flexible inner member with the rigid outer member are shown.

Figure 14:
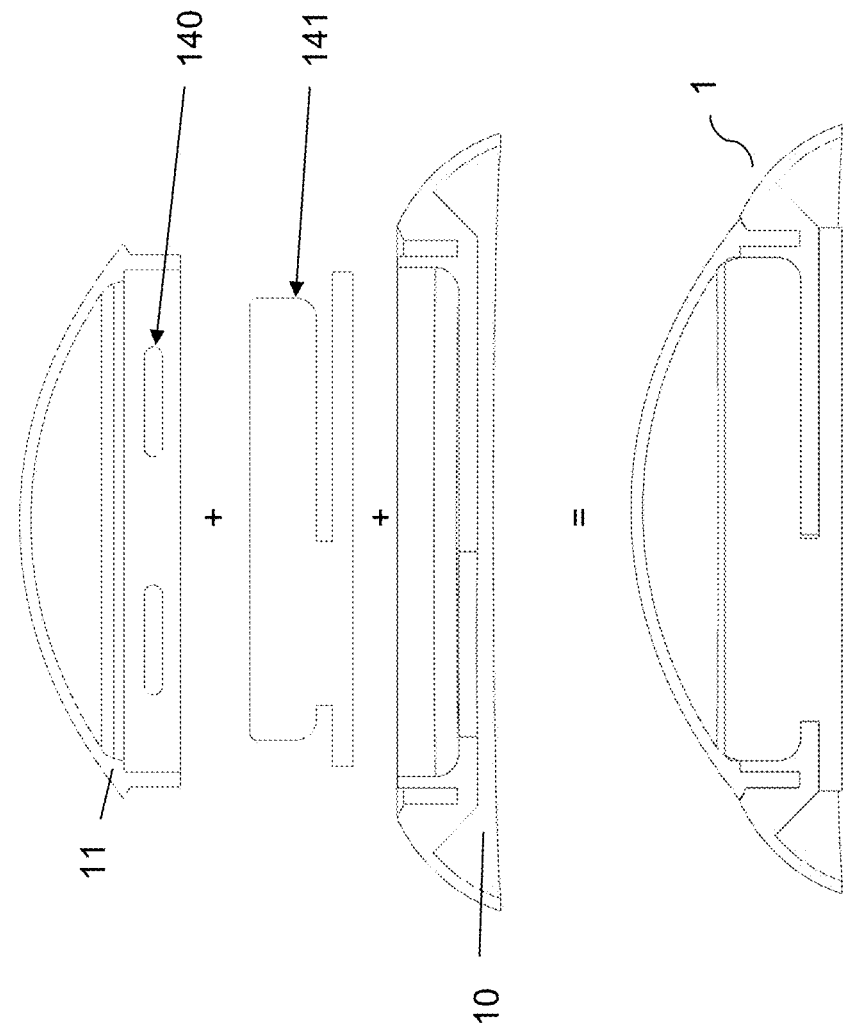
FIG. 14 shows an illustration of a sealing feature.

FIG. 14 shows an example in which the inner flexible member is overmoulded on the cup 11. The two parts could also be permanently attached together using either adhesives, welding or both, in order to form the collection vessel 1. The rigid cup includes retention features. A core 141 is used to overmould the flexible inner member together with the rigid cup.

Figure 15:
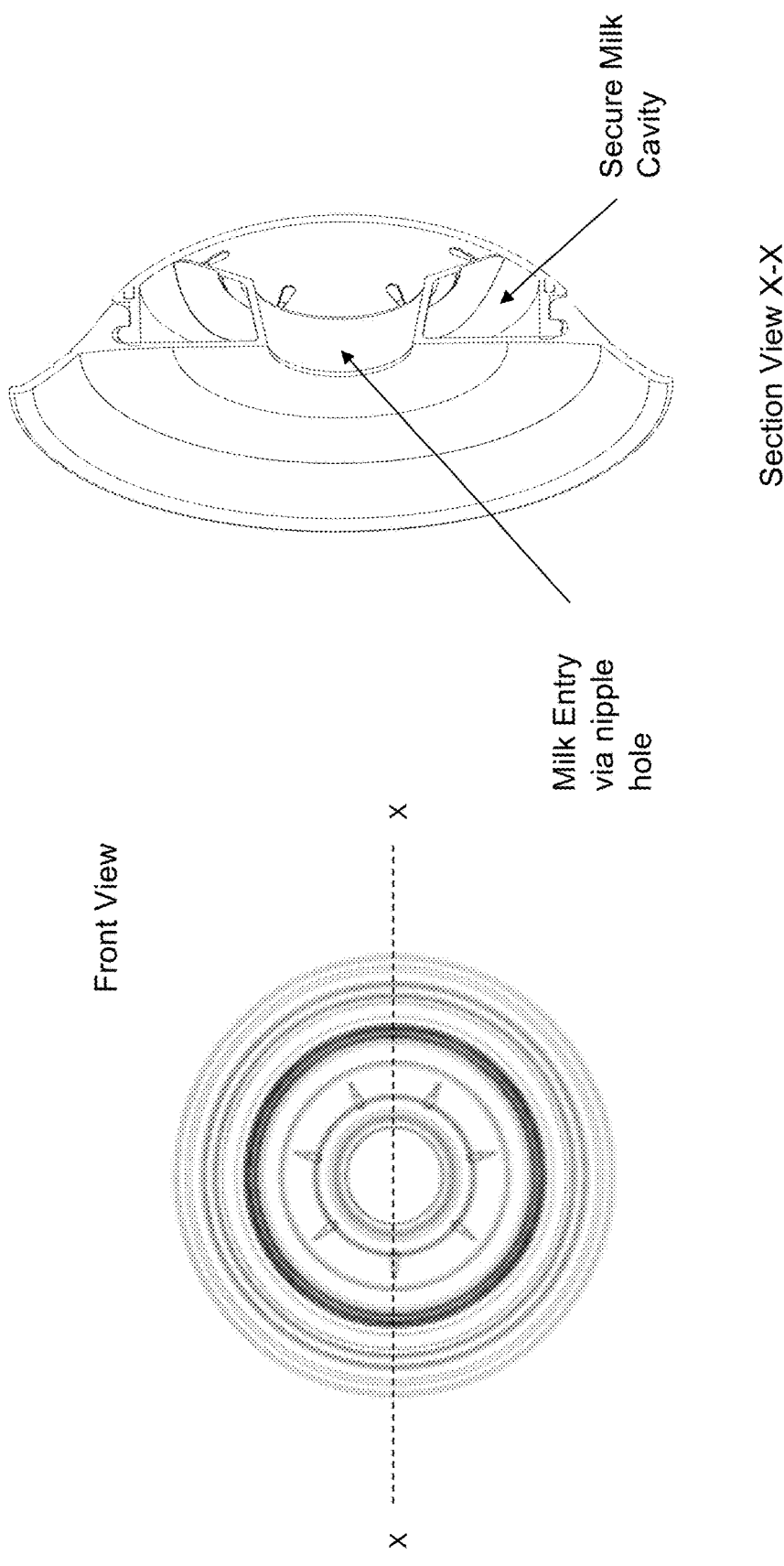
FIG. 15 shows an illustration of a sealing feature.
Figure 16:
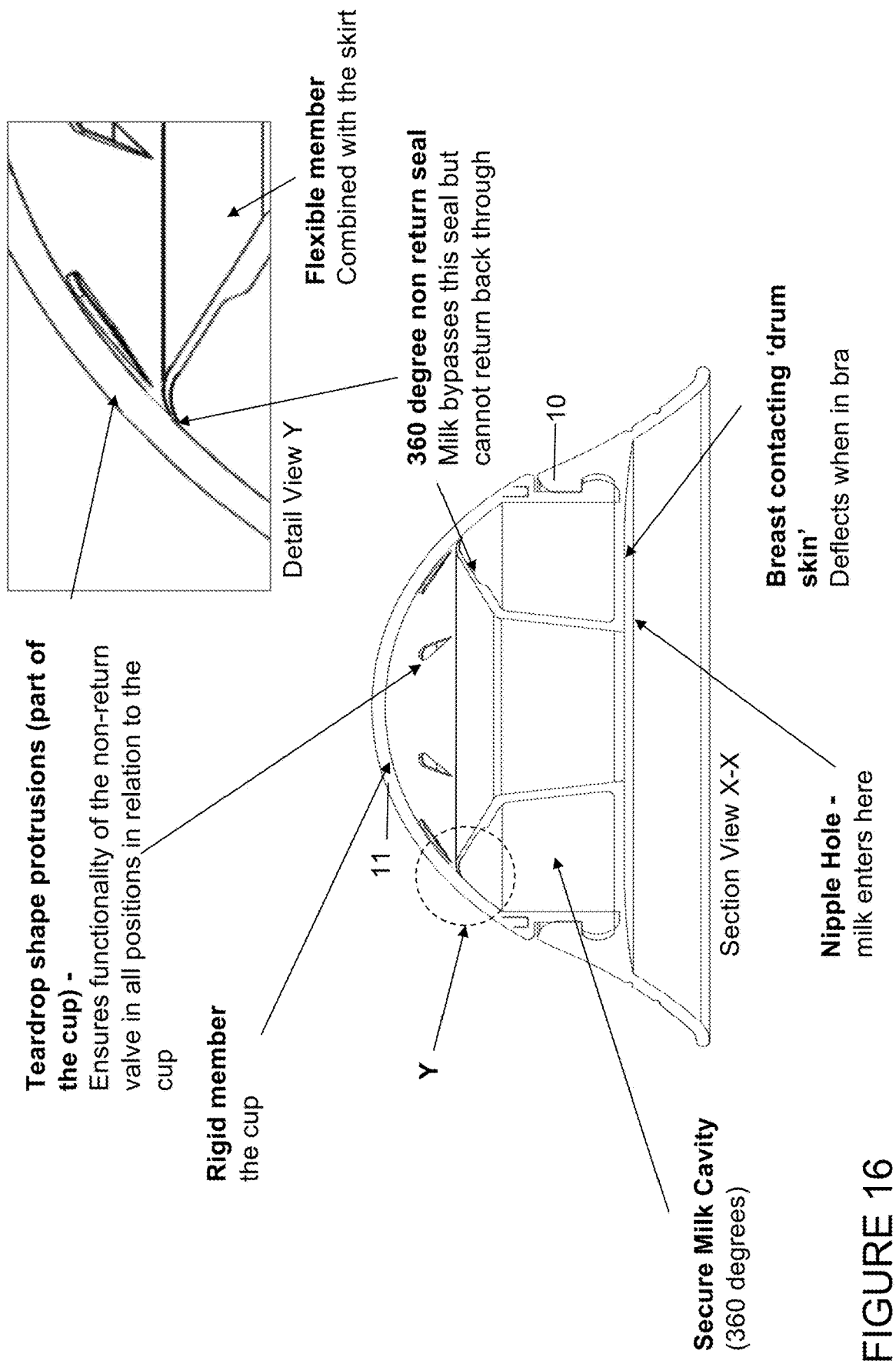
FIG. 16 shows an illustration of a sealing feature.

FIGS. 15 and 16 show a further example of collection vessel 1 providing a tortuous path for any milk letdown collected from the nipple. There are two parts to the valve. The first is an extension of the flexible skirt which sits up against the inside surface of the cup. The second is the rigid cup which has teardrop shape protrusions built into the inside surface of the cup which taper into the surface. When the collection cup is worn in a bra, the breast contacting flexible 'drum skin' deflects, which means that the circular seal can sit in a number of different locations in relation to the cup. The teardrop protrusions ensure that wherever the circular seal sits in relation to the cup, the non-return valve functions correctly by letting milk into the secure cavity and not back out. It does this by keeping the pressure head required to break the non return valve seal sufficiently low.

Figure 17:
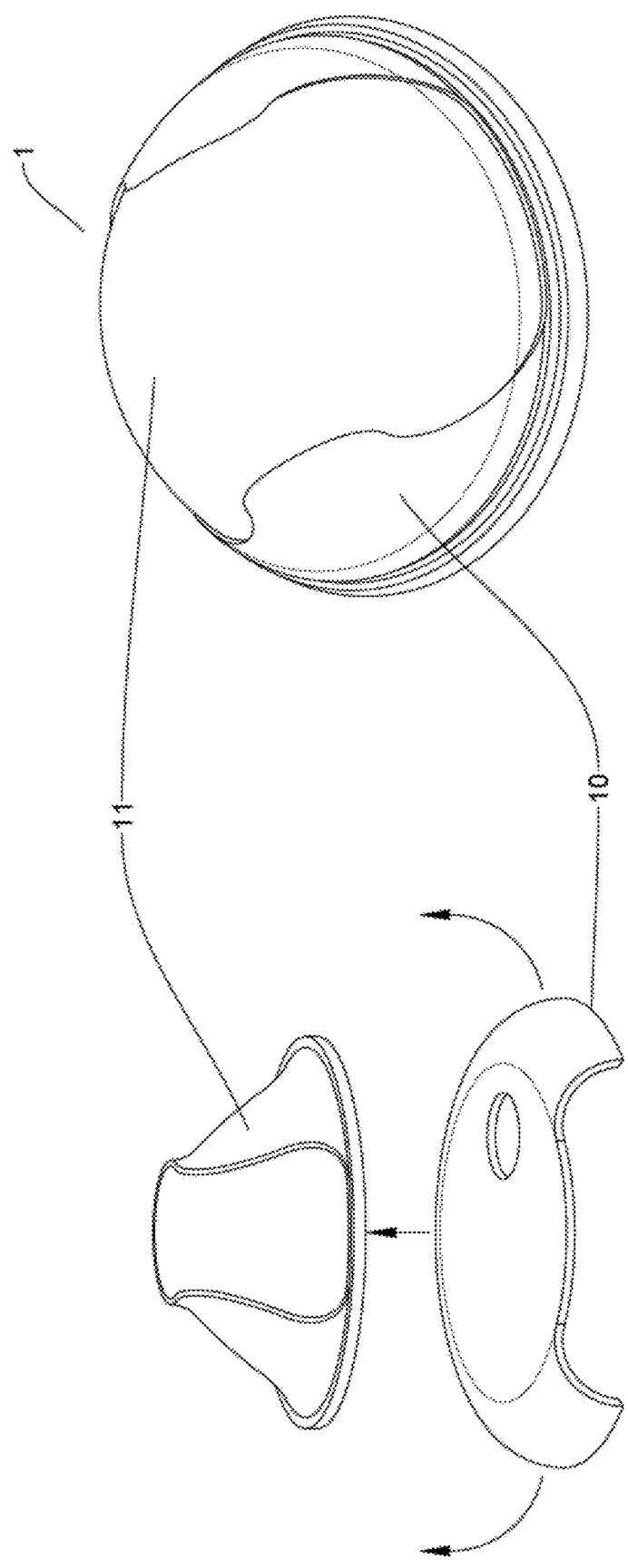
FIG. 17 shows an illustration of a sealing feature.
Figure 18:
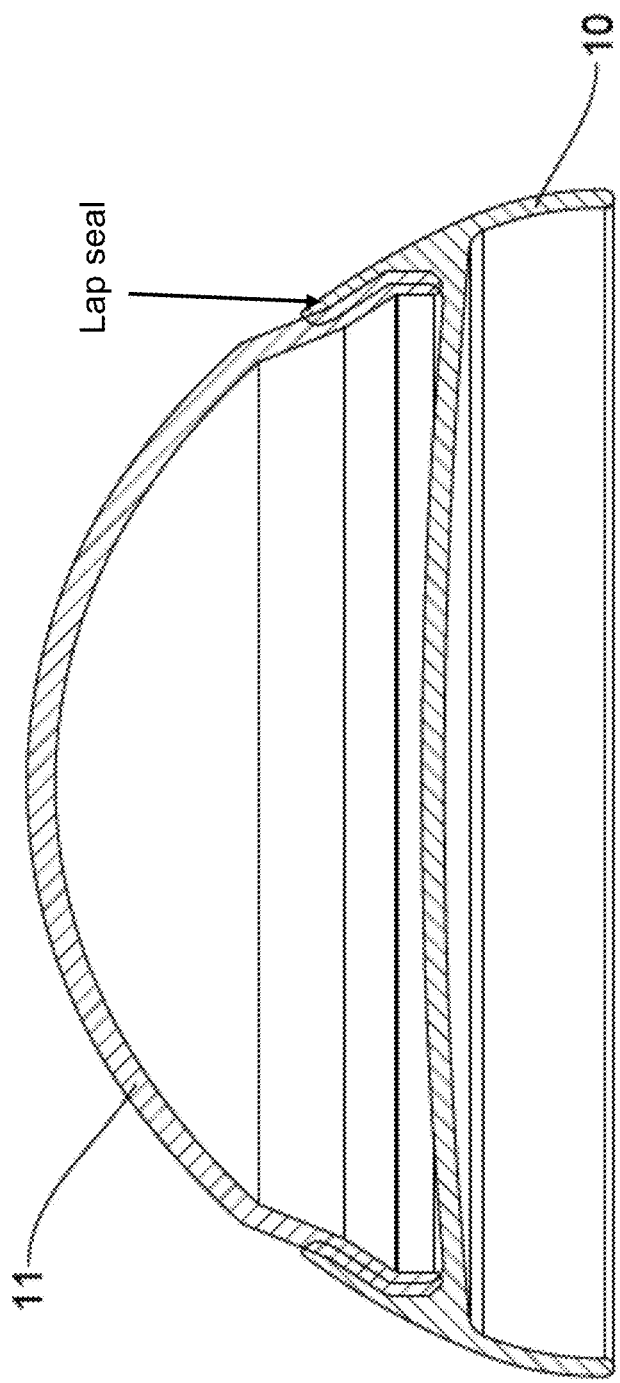
FIG. 18 shows an illustration of a sealing feature.

FIGS. 17 and 18 show another example of attachment mechanism in order to secure the flexible inner member 10 to the rigid outer member 11. The flexible inner member 'flip flaps' directly onto the rigid outer member or cup in order to provide a lap seal to secure itself onto the rigid member.

Figure 19:
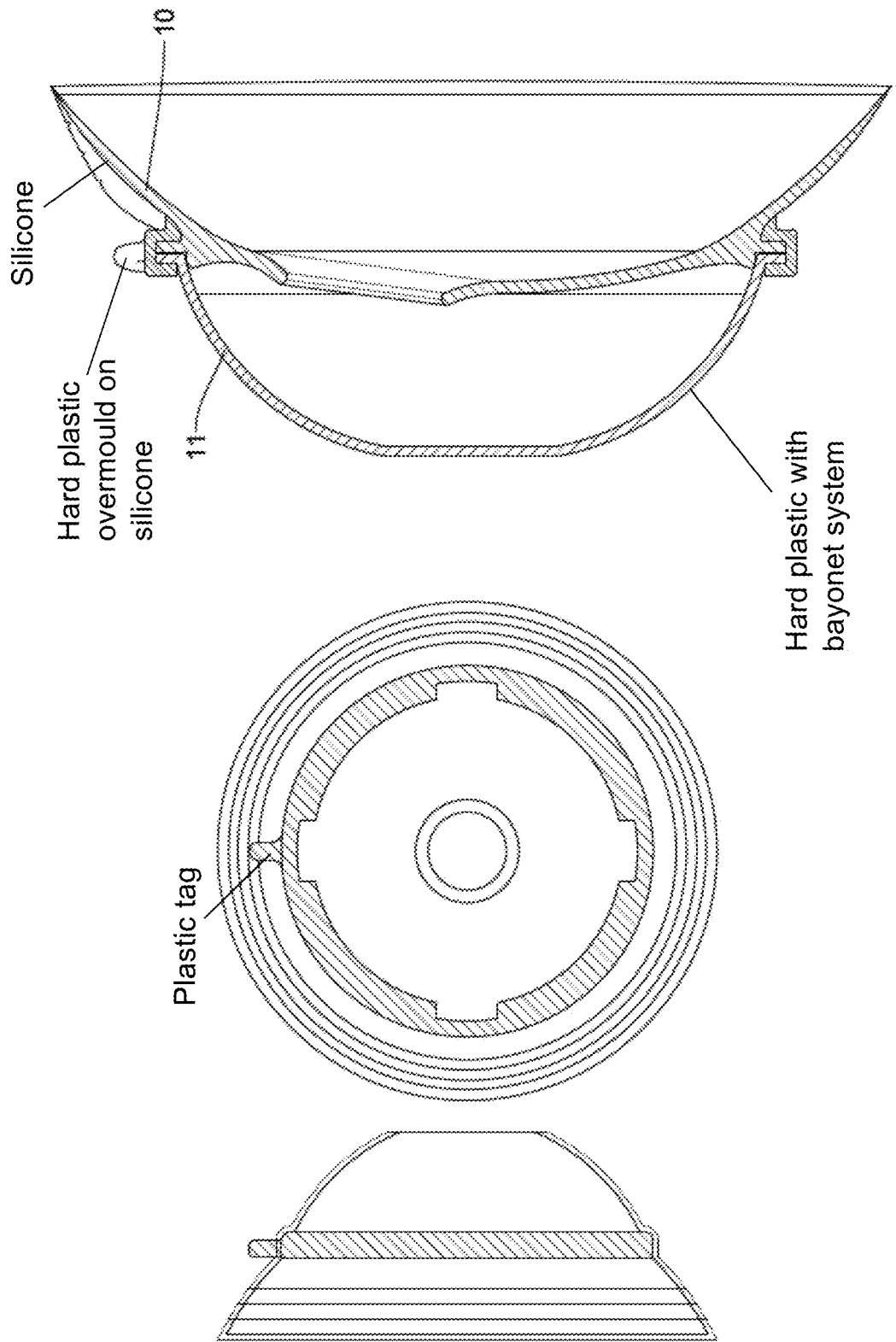
FIG. 19 shows an illustration of a sealing feature.

FIG. 19 shows a bayonet type seal in which a rigid ring is overmolded onto the silicone skirt. This sub-assembly in turn connects to the rigid cup using a push and twist action similar to a bayonet fastening which provides a leak-proof seal. To the user the product has 2 parts.

Figure 20:
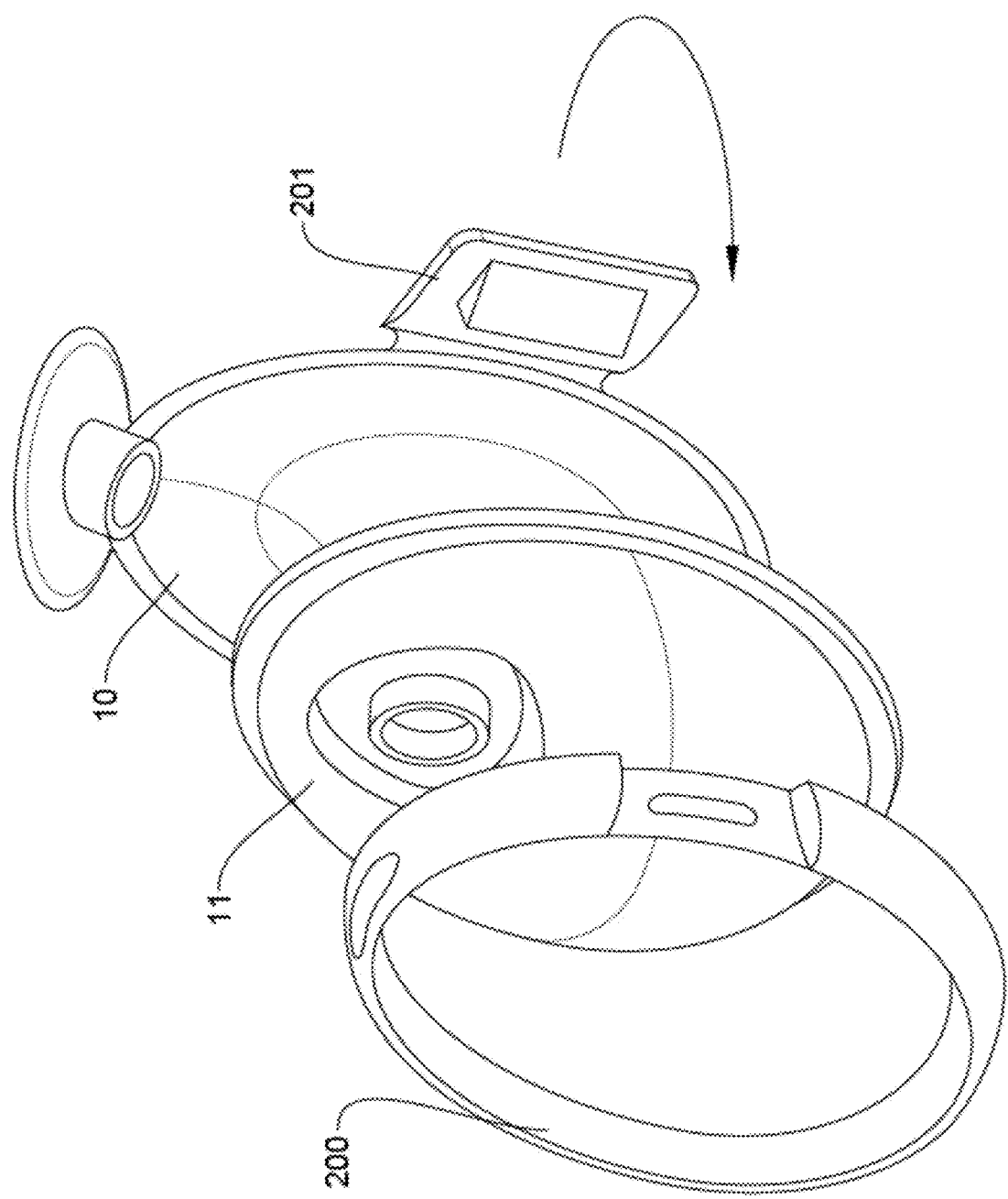
FIG. 20 shows a passive milk collection vessel including three removable parts.

With reference to FIG. 20, a passive milk collection vessel including three removable parts, namely the inner flexible member 10, the outer member 11 and an external band 200, is shown disassembled. The inner member includes a catch feature 201 that clips into place the three parts together.

Figure 21:
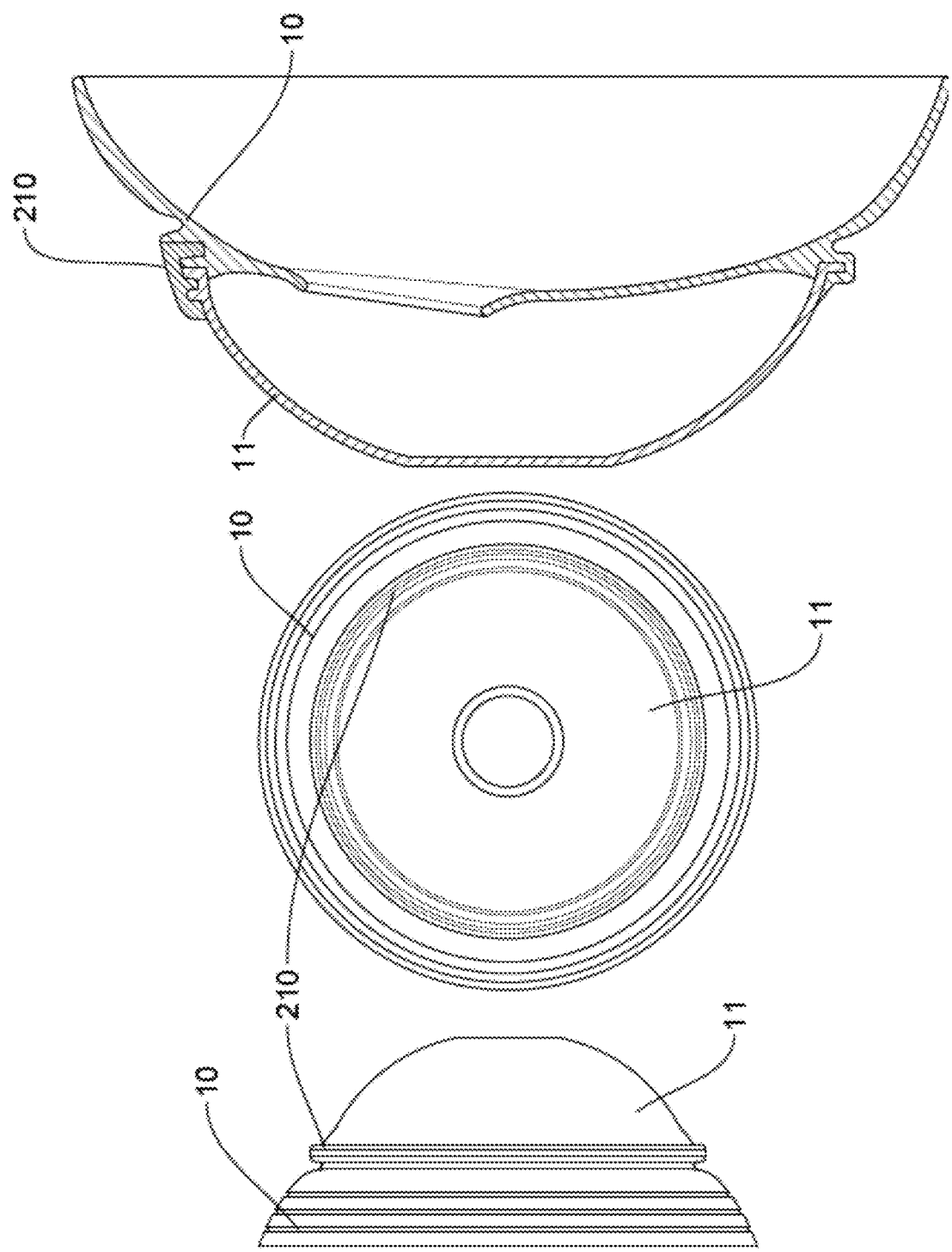
FIG. 21 shows a passive milk collection vessel including three removable parts.

With reference to FIG. 21, multiple views of another passive milk collection vessel including three removable parts, namely the inner flexible member 10, the outer member 11 and a plastic ring 210, are shown. The separate plastic part is configured to easily screw on both the flexible inner member 10 and the rigid outer member 11, thereby providing a secure seal between the flexible inner member 10 and rigid outer member 11.

Figure 22:
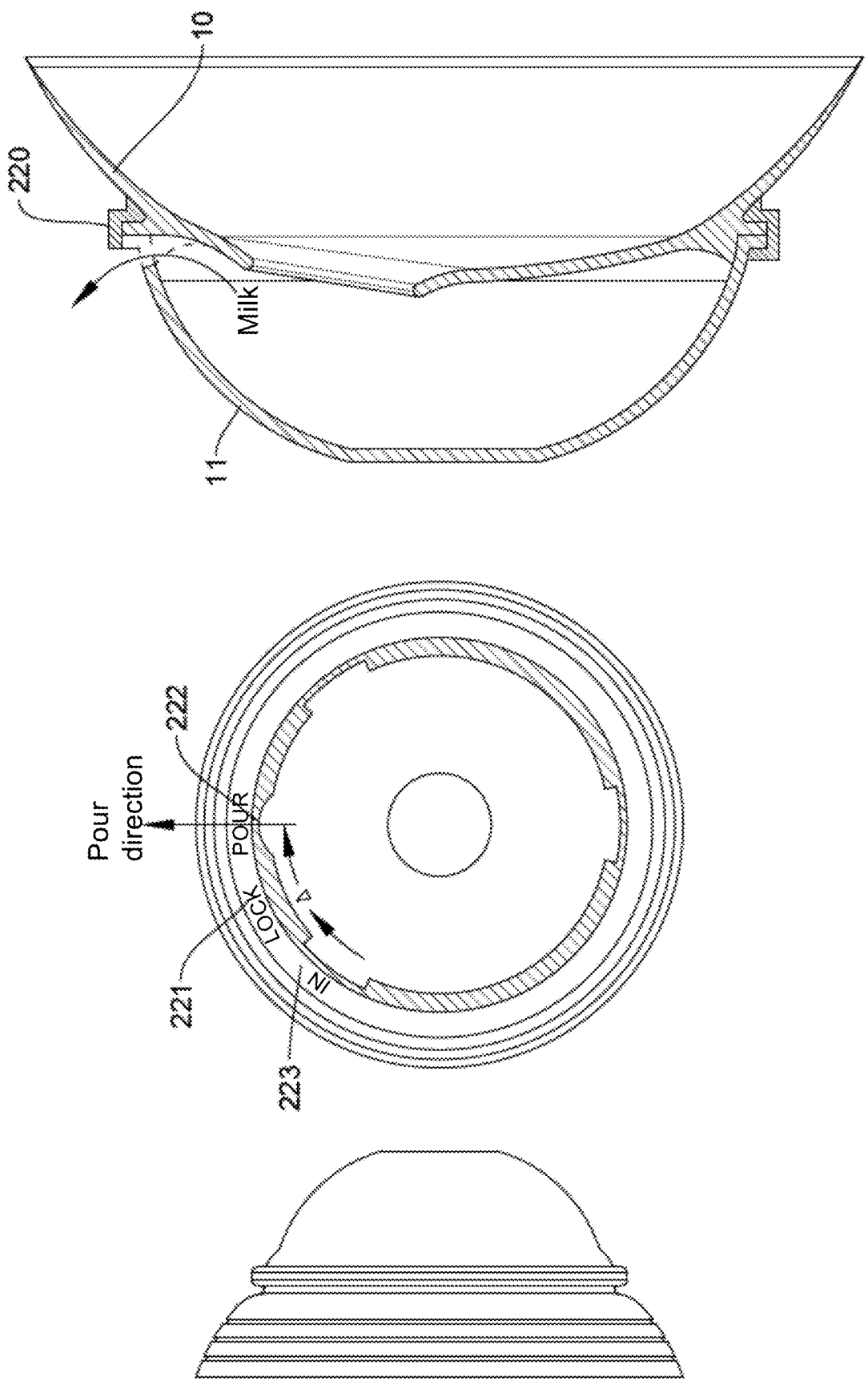
FIG. 22 shows a passive milk collection vessel including three removable parts.

With reference to FIG. 22, multiple views of another passive milk collection vessel including three parts, namely the inner flexible member 10, the outer member 11 and a rigid ring 220, are shown. The rigid ring 220 is overmolded and includes an inner part in silicone and an outer part in hard plastic. Further the rigid ring 220 is configured to rotate in order to provide multiple functions. A 'lock' position 221 provides a secure seal when the device is placed and sealed on the breast. A 'pour' milk position 222 provides an opening on the ring in order to easily decant milk out of the device. An 'in' position 223 indicates where to place the rigid ring on the inner and outer members.

Figure 23:
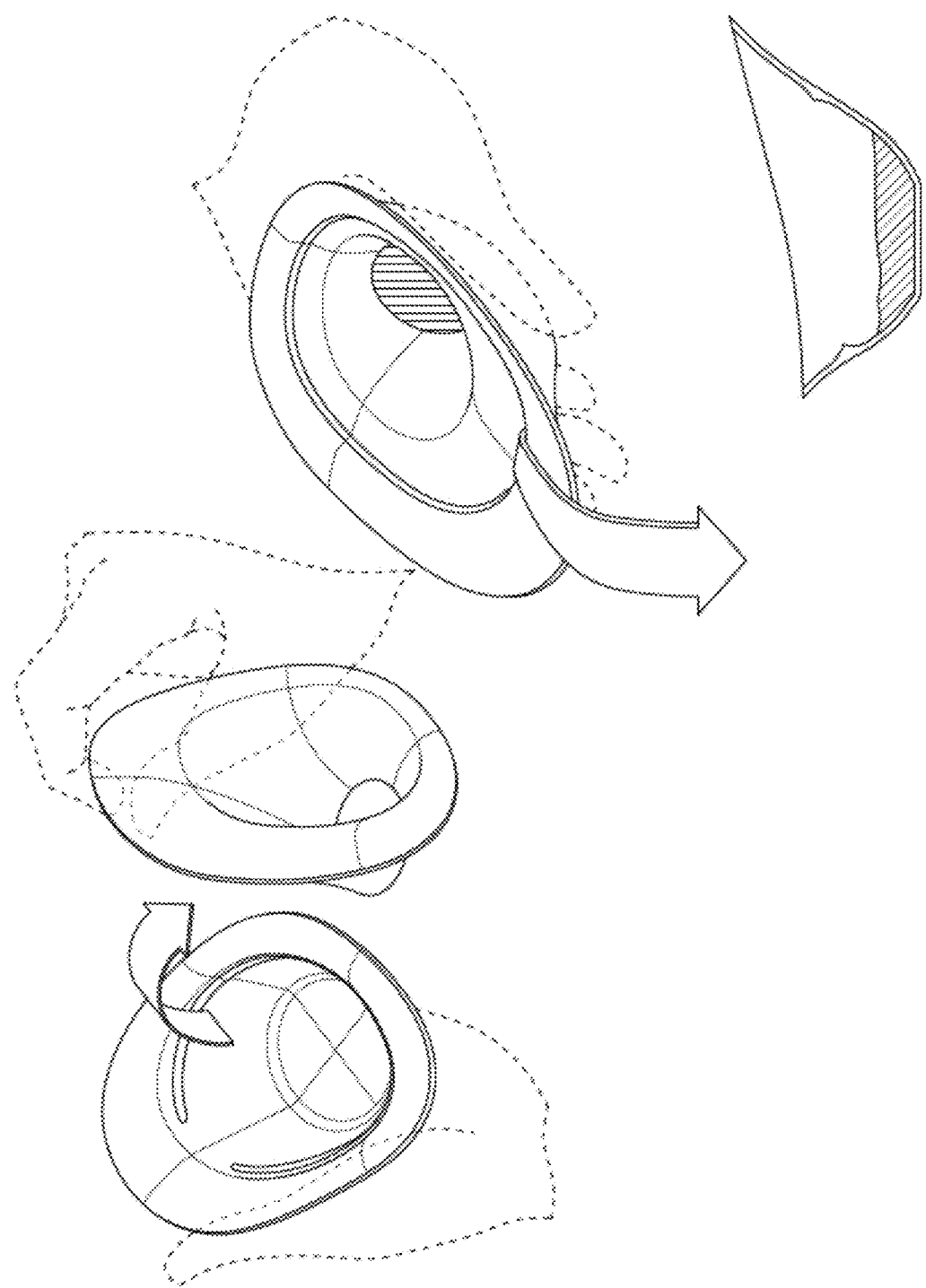
FIG. 23 shows an example of a milk decanting feature.
Figure 24:
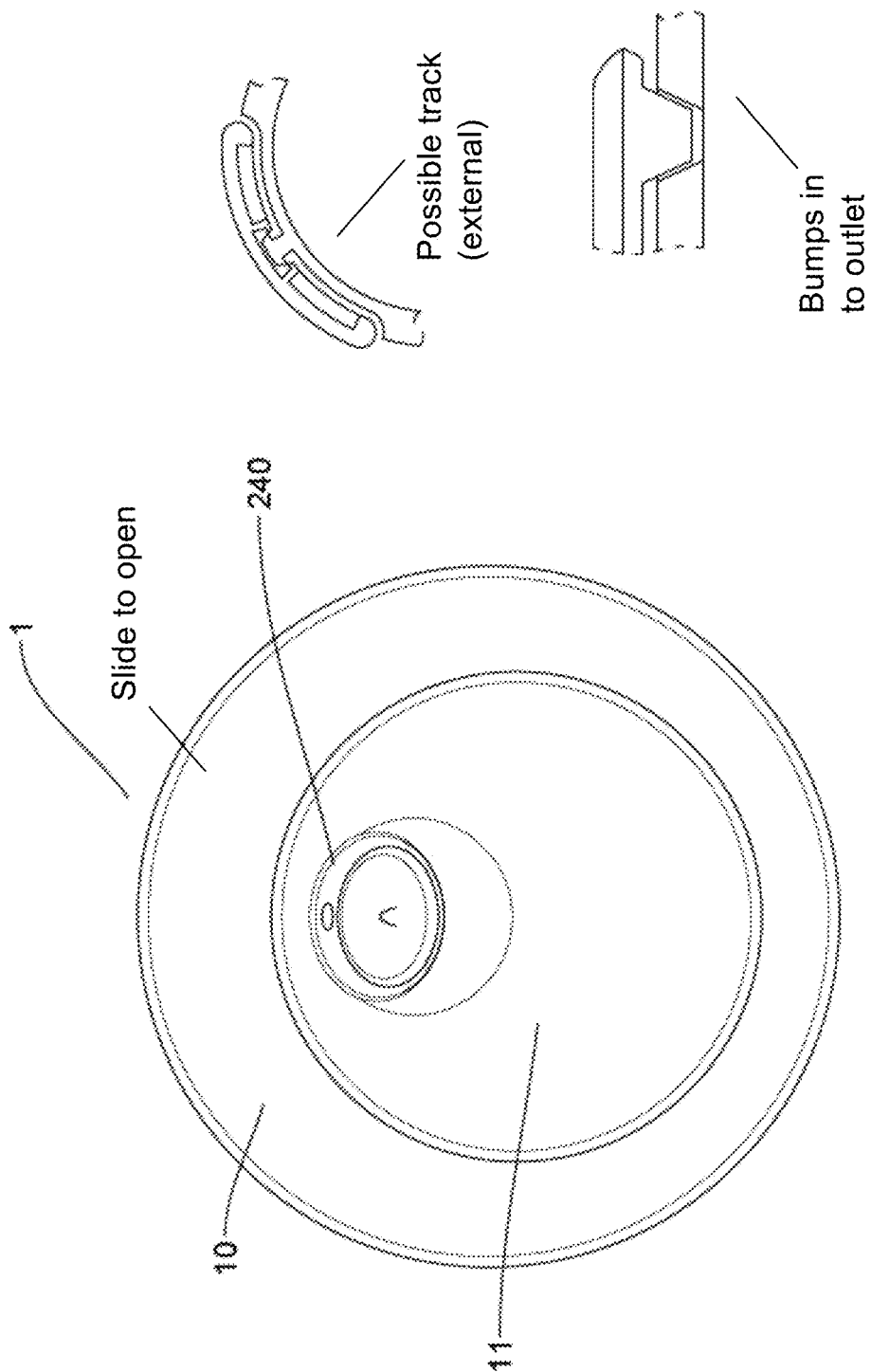
FIG. 24 shows an example of a milk decanting feature.
Figure 25:
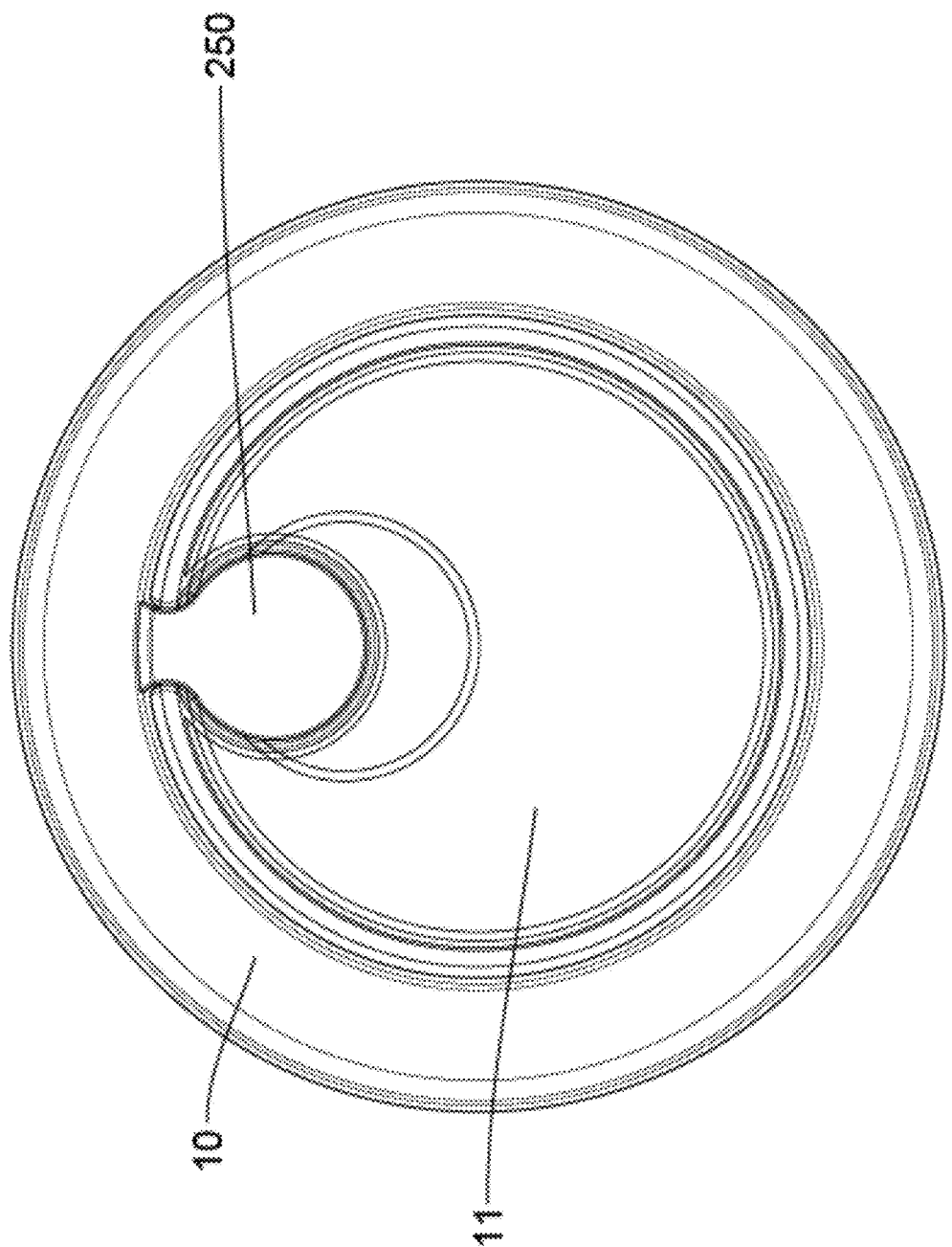
FIG. 25 shows an example of a milk decanting feature.

With reference to FIGS. 23 to 25, further examples of milk decanting alternatives are illustrated.

FIG. 23 shows a second opening or hole located at the top of the silicone inner member. When the device is worn, the second opening seals against the user's breast and is therefore closed. When the device is taken off the breast, the second opening provides a pouring spout with which to easily decant the milk out of FIG. 24 shows a collection vessel in which the rigid cup includes an outlet on its outer surface and an integrated bung. The bung can be open in order to decant any collected milk via the outlet.

FIG. 25 shows a collection vessel in which the rigid cup includes an opening to decant collected milk. The collection vessel also includes a bung that is directly integrated to the flexible inner member and which can be opened in order to decant any collected milk.

Figure 26:
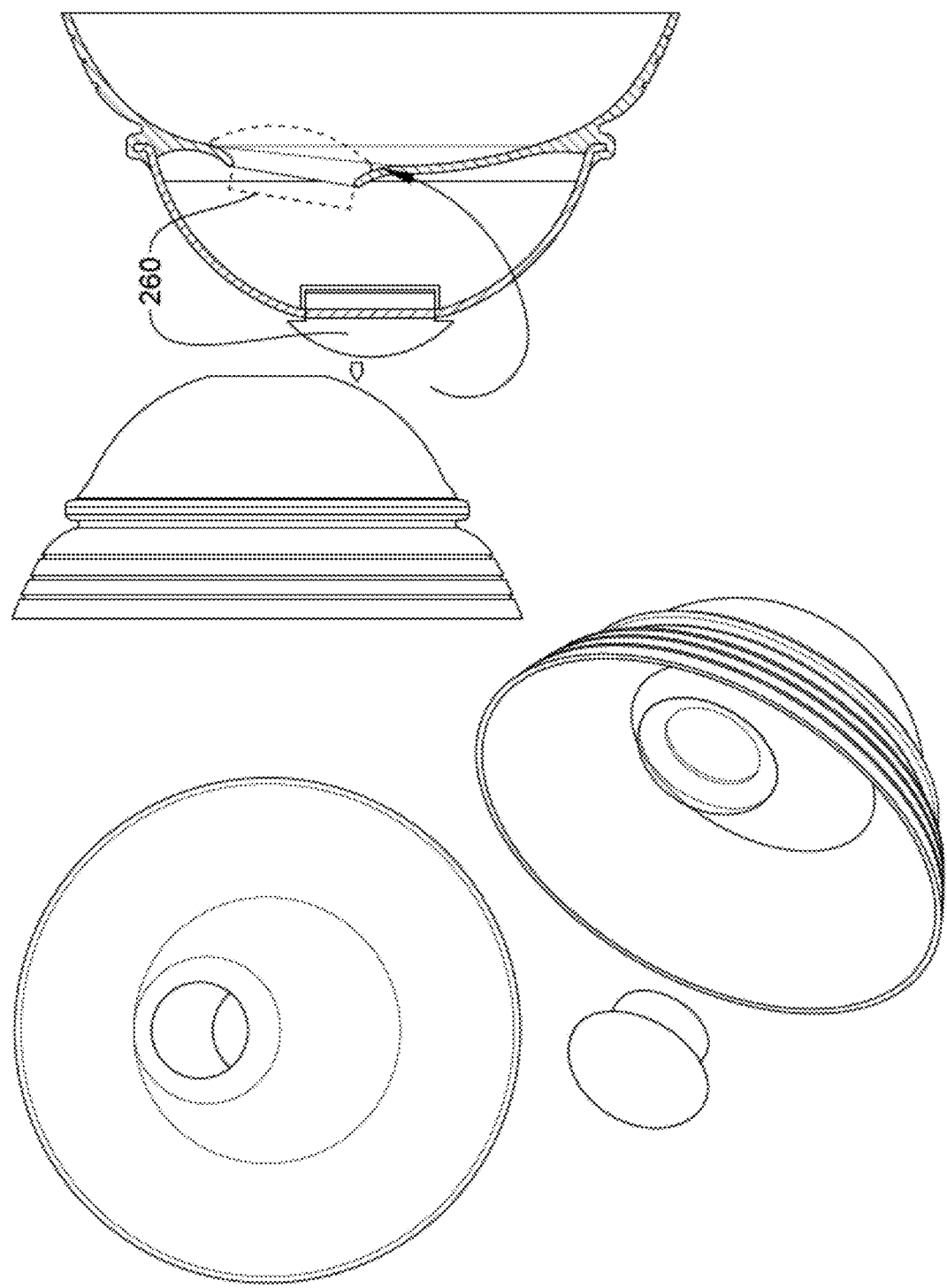
FIG. 26 shows a collection vessel comprising a bung or stopper cap is attached on or externally to the rigid cup.

FIG. 26 shows a collection vessel comprising a bung or stopper cap that is attached on or outside of the rigid cup. The stopper cap 260 can be pushed inwards and onto the nipple hole of the flexible inner member in order to seal the nipple hole. When the nipple hole is sealed, the collection vessel may be used as a storage vessel.

Figure 27:
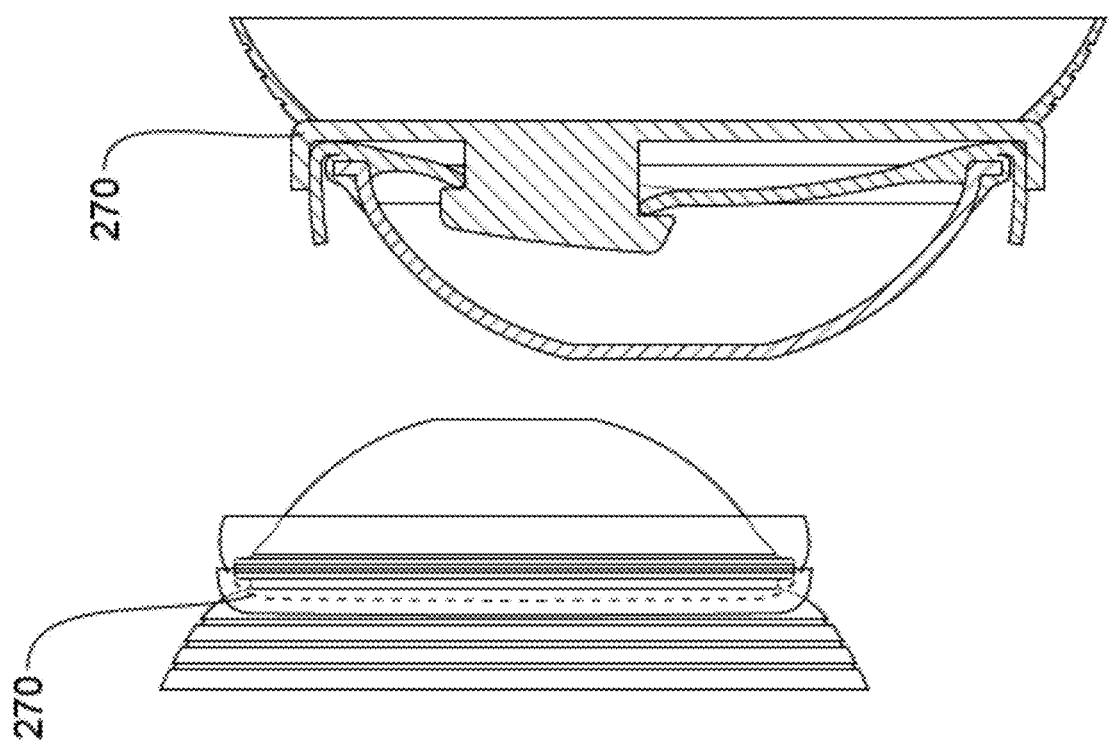
FIG. 27 shows a collection vessel including a cap with a plug.

FIG. 27 shows a collection vessel including a cap with a plug, in which the cap is placed on or near the rear surface of the inner member in order to seal the nipple hole. The cap also attaches or clips onto the rigid cup. In this example, the flexible inner member includes a flippable portion.

Figure 28:
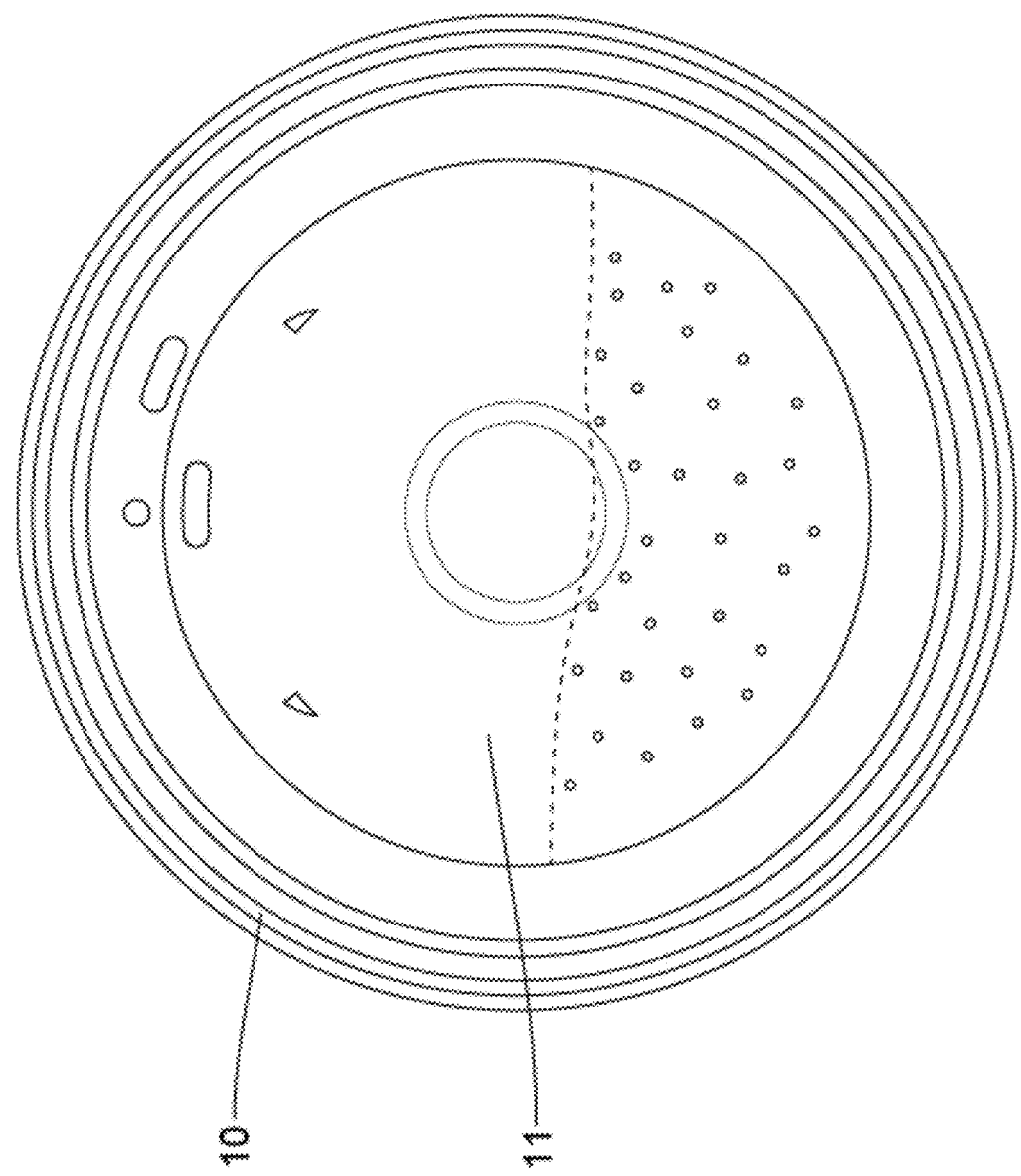
FIG. 28 shows a collection vessel in which the rear surface of the rigid cup provides a visual indication or marker of the maximum level of milk let-down which can be collected inside the cup.

FIG. 28 shows a collection vessel in which the outer surface of the rigid cup provides a visual indicator or marker of the maximum level of milk let-down that can be collected inside the cup. The visual indicator or marker may be provided using a specific texture, such as frosted plastic, on the rigid cup. An additional visual indicator may be provided in order for the user to understand if the device is either in a locked or unlocked position.

Figure 29:
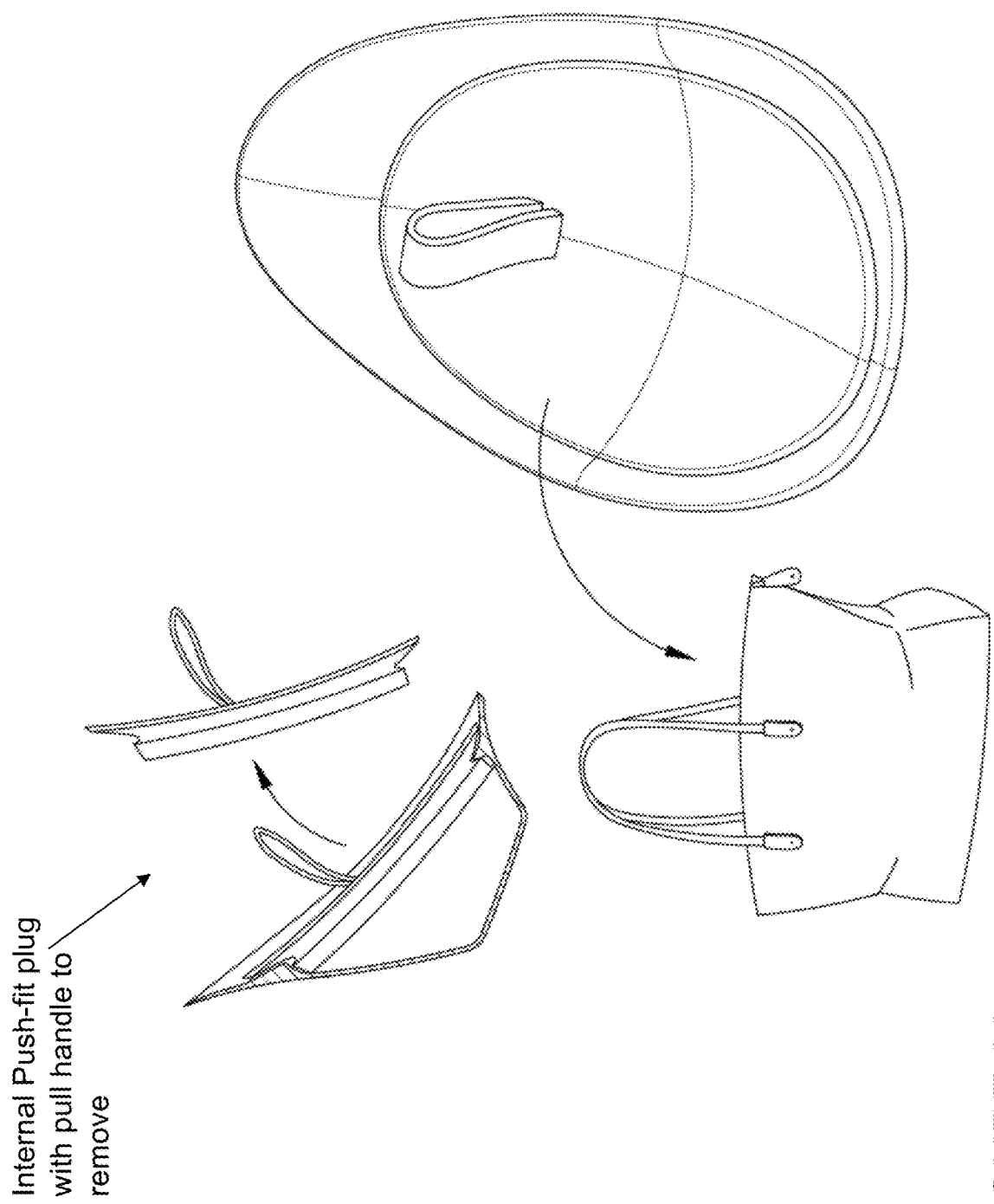
FIG. 29 shows a collection vessel further including a push-fit plug.

FIG. 29 shows a collection vessel further including a push-fit plug. The plug is used to close the nipple hole and enables the collection vessel to be used as a storage container. The plug includes a pull handle enabling the vessel to be easily carried around, such as being placed or removed from a bag.

Figure 30:
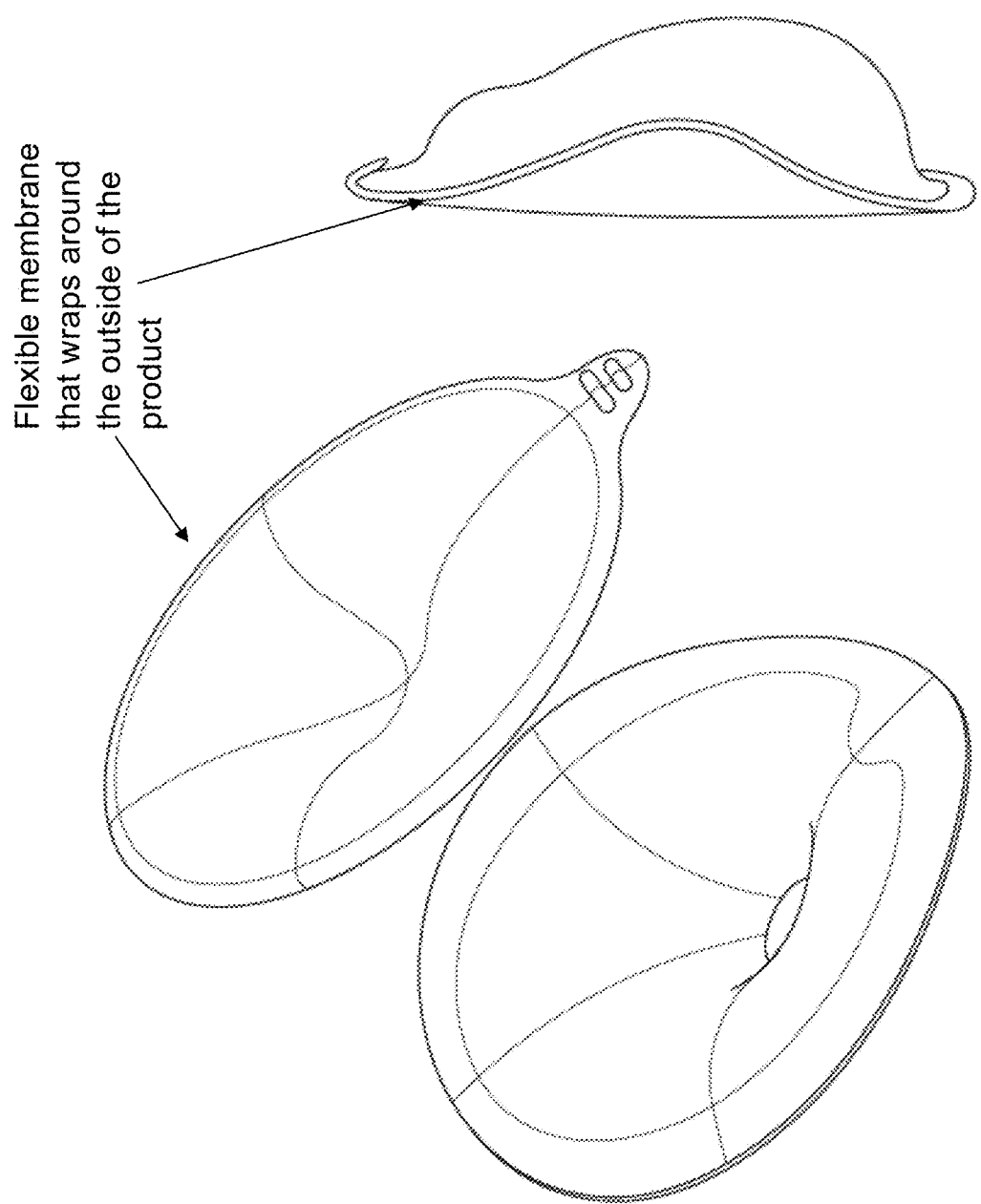
FIG. 30 shows a collection vessel further including a flexible membrane that is shaped to wrap around at least a portion of the vessel.

FIG. 30 shows a collection vessel further including a flexible membrane that is shaped to wrap around at least a portion of the vessel. The flexible membrane closes the nipple area and enables the vessel to be easily transported or to be stored in a fridge.

Key Features

An aspect of the invention is a passive milk collection device for storing milk comprising (i) a flexible inner member including a nipple hole for receiving a nipple, and in which, in use, part of the rear surface of the inner member is configured to securely seal onto a user's breast and (ii) a removable rigid outer member configured to attach onto the front surface of the inner member and to provide a free air space around the nipple area for storing milk from the nipple, and in which, the circumference of the outer edge of the rear surface of the flexible inner member is substantially larger than the circumference of the rigid outer member.

Optional features are now listed. Note that all optional features can be combined with any other optional features.

Flexible Inner Member

Part of the rear surface of the flexible inner member around or near the nipple hole seals or self-seals against the breast, providing a generally leak proof milk collection vessel.

Flexible inner member in use provides a substantially continuous contour or surface with the breast.

Flexible inner member is made substantially of a soft silicone.

Flexible inner member is configured at least in part to deform outwards when pressed against the breast to create a low negative air pressure inside the device sufficient to adhere the device to the breast.

Flexible inner member is stable in two different orientations: a first orientation in which it continues the curve of the outer member; and a second orientation in which it is flipped back through at least 45 degrees and preferably at least 90 degrees.

Flexible inner member includes one or more ventilation holes or openings.

Ventilation hole or opening is configured to be plugged using an elastic feature built into the inner member, or a separate plugging member.

The flexible inner member is shaped or configured to fit comfortably against the breast.

The flexible inner member is not circular in a frontal view but elongated at the top.

The flexible inner member is not circular in a frontal view but truncated or flattened at its base.

The rear or outermost edge of the inner member is not parallel with the rear edge of the central outer member, but instead the top of the rear or outermost edge of the inner member is further away from the rear edge of the central outer member than the bottom of the edge of the skirt.

Nipple Hole
  Nipple hole is configured to comfortably seal against the breast around the nipple area.
  Nipple hole has an asymmetrical shape.
  Nipple hole has a non-circular shape.
  Nipple hole is configured to allow easy pouring of collected milk out of the device.
  Nipple hole is configured to maximise the milk collection volume of the device.
  Nipple hole is configured to allow a choice of fit orientation for comfort and integration to the varying breast forms.
  Nipple hole is located, in use, above the height mid-point line of the rear surface of the inner member.
Rigid Outer Member
  Rigid outer member is configured to collect any let-down milk.
  Outer member is made substantially of an optically clear material.
  Outer member has a generally convex outer surface.
  Outer member is pressed or pushed into engagement with the inner member such that the inner member holds the outer member firmly and securely in position.
  The outer member interference fit seals against the inner member.
  An attachment mechanism is configured to retain the outer member in attachment with the inner member.
  An attachment mechanism is one or more of the following: hook, lip, latch, or bump feature.
  A retention hook extends transversely around or near a periphery of the front surface of the inner member.
  A sealing lip extends transversely around or near a periphery of the front surface of the inner member.
  A bump feature extends transversely around or near an internal periphery of the inner member.
  Outer member includes a flat portion so that the entire device can rest stably on its front on a surface, while preventing any milk spillage.
Whole Device
  Device is configured to substantially fit inside a bra.
  Entire device is substantially transparent.
  Entire device is skin coloured.
  The device is shaped to conform with the shape of a 'tear-drop' breast shape, thereby providing a discreet profile when attached onto the breast.
  The device has a milk capacity of approximately 1 US fluid ounce or 30 ml.

NOTE

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred example(s) of the invention, it will be apparent to those of ordinary skill in the art that numerous modifications can be made without departing from the principles and concepts of the invention as set forth herein.

The invention claimed is:

1. A passive milk collection device for storing milk comprising:
a flexible inner member comprising a front surface, a rear surface, and a nipple hole configured to receive a nipple, wherein in use, at least part of the rear surface of the inner member is configured to securely seal onto a user's breast; and
a removable rigid outer member configured to attach onto the front surface of the inner member and to provide a free air space around the nipple area for storing milk from the nipple, wherein the circumference of an outer edge of the rear surface of the flexible inner member is larger than the circumference of the rigid outer member.

2. The device of claim 1, wherein at least part of the rear surface of the flexible inner member around or near the nipple hole is configured to seal or self-seal against the breast.

3. The device of claim 1, wherein the flexible inner member is configured to, in use, provide a substantially continuous contour or surface with the breast.

4. The device of claim 1, wherein the flexible inner member is configured at least in part to deform outwards when pressed against the breast to create a low negative air pressure inside the device sufficient to adhere the device to the breast.

5. The device of claim 1, further comprising one or more ventilation holes or openings.

6. The device of claim 5, wherein the ventilation hole or opening is configured to be plugged using an elastic feature built into the inner member, or a separate plugging member.

7. The device of claim 1, wherein the flexible inner member is not circular.

8. The device of claim 1, wherein a rear or outermost edge of the inner member is not parallel with a rear edge of the outer member, but instead a top of the rear or outermost edge of the inner member is further away from the rear edge of the outer member than a bottom of the edge of the inner member.

9. The device of claim 1, wherein the nipple hole comprises an asymmetrical shape.

10. The device of claim 1, wherein the nipple hole is located, in use, above the height mid-point line of the rear surface of the inner member.

11. The device of claim 1, wherein the outer member is configured to collect let-down milk.

12. The device of claim 1, wherein the outer member comprises a convex outer surface.

13. The device of claim 1, wherein the outer member is configured to be pressed or pushed into engagement with the inner member such that the inner member retains the outer member.

14. The device of claim 1, wherein the outer member is configured to seal against the inner member.

15. The device of claim 1, further comprising an attachment is configured to retain the outer member in attachment with the inner member.

16. The device of claim 1, wherein a sealing lip extends transversely around or near a periphery of the front surface of the inner member.

17. The device of claim 1, wherein a bump feature extends transversely around or near an internal periphery of the inner member.

18. The device of claim 1, wherein the outer member includes a flat portion configured to allow the device to rest on its front on a surface.

19. The device of claim 1, wherein the device is configured to substantially fit inside a bra.

20. The device of claim 1, wherein the device is substantially transparent.

* * * * *